US011654135B2

(12) United States Patent
Christiano

(10) Patent No.: US 11,654,135 B2
(45) Date of Patent: May 23, 2023

(54) METHODS FOR TREATING COLON CANCER WITH COMPOSITIONS COMPRISING AMLEXANOX AND IMMUNE CHECKPOINT INHIBITORS

(71) Applicant: MOONSHOT PHARMA LLC, New York, NY (US)

(72) Inventor: Angela Christiano, Mahwah, NJ (US)

(73) Assignee: Moonshot Pharma LLC, New York, NY (US)

( * ) Notice: Subject to any disclaimer, the term of this patent is extended or adjusted under 35 U.S.C. 154(b) by 279 days.

(21) Appl. No.: 16/623,696

(22) PCT Filed: Jun. 22, 2018

(86) PCT No.: PCT/US2018/039102
§ 371 (c)(1),
(2) Date: Dec. 17, 2019

(87) PCT Pub. No.: WO2018/237326
PCT Pub. Date: Dec. 27, 2018

(65) Prior Publication Data
US 2020/0155519 A1 May 21, 2020

Related U.S. Application Data

(60) Provisional application No. 62/523,537, filed on Jun. 22, 2017.

(51) Int. Cl.
*A61K 31/436* (2006.01)
*A61P 35/00* (2006.01)
*A61K 39/395* (2006.01)
*A61K 39/00* (2006.01)
*A61K 45/06* (2006.01)

(52) U.S. Cl.
CPC ........ *A61K 31/436* (2013.01); *A61K 39/3955* (2013.01); *A61K 45/06* (2013.01); *A61P 35/00* (2018.01); *A61K 2039/507* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 4,708,871 A | 11/1987 | Geysen | |
| 4,833,092 A | 5/1989 | Geysen | |
| 5,223,409 A | 6/1993 | Ladner et al. | |
| 5,403,484 A | 4/1995 | Ladner et al. | |
| 5,427,908 A | 6/1995 | Dower et al. | |
| 5,432,108 A | 7/1995 | Lee | |
| 5,498,530 A | 3/1996 | Schatz et al. | |
| 5,556,762 A | 9/1996 | Pinilla et al. | |
| 5,571,689 A | 11/1996 | Heuckeroth et al. | |
| 5,580,717 A | 12/1996 | Dower et al. | |
| 5,624,821 A | 4/1997 | Winter et al. | |
| 5,648,260 A | 7/1997 | Winter et al. | |
| 5,663,143 A | 9/1997 | Ley et al. | |
| 5,698,426 A | 12/1997 | Huse | |
| 5,723,286 A | 3/1998 | Dower et al. | |
| 5,723,323 A | 3/1998 | Kauffman et al. | |
| 5,734,018 A | 3/1998 | Rutter et al. | |
| 5,750,373 A | 5/1998 | Garrard et al. | |
| 5,763,192 A | 6/1998 | Kauffman et al. | |
| 5,770,434 A | 6/1998 | Huse | |
| 6,992,096 B2 | 1/2006 | Karp et al. | |
| 8,163,782 B2 | 4/2012 | Karp et al. | |
| 8,227,494 B2 | 7/2012 | Karp et al. | |
| 8,716,321 B2 | 5/2014 | Hirawat et al. | |
| 8,796,322 B2 | 8/2014 | Karp et al. | |
| 2004/0214193 A1 | 10/2004 | Eisenlohr et al. | |
| 2006/0166926 A1 | 7/2006 | Wilde et al. | |
| 2006/0167263 A1 | 7/2006 | Wilde et al. | |
| 2007/0135473 A1 | 6/2007 | Semov et al. | |
| 2007/0203123 A1 | 8/2007 | Wilde et al. | |
| 2008/0207538 A1 | 8/2008 | Lawrence et al. | |
| 2009/0032592 A1 | 2/2009 | Christensen | |

(Continued)

FOREIGN PATENT DOCUMENTS

JP 2006340714 A 12/2006
WO 1984003506 A1 9/1984

(Continued)

OTHER PUBLICATIONS

Anonymous—List of cancer types. https://en.wikipedia.org/wiki/List_of_cancer_types—accessed May 22, 2020. (Year: 2020).*
NCI—https://www.cancer.gov/about-cancer/understanding/what-is-cancer. (Year: 2020).*
Loudon et al. Repurposing Amlexanox as a 'Run the Red-Light Cure-All' with Readthrough—a 'No-Nonsense' Approach to Personalized Medicine. J. Bioanal. Biomed., 5, 79-96, 2013. (Year: 2013).*
Callahan et al., CTLA-4 and PD-1 pathway blockade: combinations in the clinic. Frontiers in Oncology, 4, article 385, 1-6, 2015. (Year: 2015).*

(Continued)

*Primary Examiner* — Elly-Gerald Stoica
(74) *Attorney, Agent, or Firm* — Troutman Pepper Hamilton Sanders LLP

(57) ABSTRACT

Disclosed herein are compositions and methods for treating cancer in a subject. In some embodiments, the methods involve generating an immune response in an individual by inducing the expression of neoantigens on the surface of abnormal (such as proliferative) cells. In one embodiment, a method of treating cancer in a subject includes administering amlexanox in combination with immune modulators, such as checkpoint inhibitors, immune co-stimulatory molecules, TLR agonists, and TNFR superfamily agonists. In one embodiment, the checkpoint inhibitors are selected from antibodies against PD-1, PD-L1, and CTLA-4.

6 Claims, 4 Drawing Sheets

(56) References Cited

U.S. PATENT DOCUMENTS

| | | |
|---|---|---|
| 2009/0149513 A1 | 6/2009 | Hirawat et al. |
| 2009/0203752 A1 | 8/2009 | Campbell et al. |
| 2010/0093867 A1 | 4/2010 | Matsuda et al. |
| 2011/0003843 A1 | 1/2011 | Lejeune et al. |
| 2011/0046136 A1 | 2/2011 | Almstead et al. |
| 2012/0087896 A1 | 4/2012 | Almstead et al. |
| 2012/0263740 A1 | 10/2012 | Gilboa et al. |
| 2013/0217717 A1 | 8/2013 | Lejeune et al. |
| 2013/0224237 A1 | 8/2013 | Gilboa |
| 2013/0289007 A1 | 10/2013 | Karp et al. |
| 2013/0293637 A1 | 11/2013 | Bacon et al. |
| 2014/0094457 A1 | 4/2014 | Gardner et al. |
| 2015/0051251 A1 | 2/2015 | Gatti et al. |
| 2015/0202223 A1* | 7/2015 | Lee ..................... C12Q 1/6883 514/183 |
| 2015/0274674 A1 | 10/2015 | Almstead et al. |
| 2015/0290207 A1 | 10/2015 | Kutok et al. |
| 2016/0015709 A1 | 1/2016 | Cheresh et al. |
| 2017/0226221 A1 | 8/2017 | Madiyalakan et al. |
| 2019/0083489 A1 | 3/2019 | Christiano |

FOREIGN PATENT DOCUMENTS

| | | |
|---|---|---|
| WO | 1984003564 A1 | 9/1984 |
| WO | 1994029351 A2 | 12/1994 |
| WO | 1997015390 A1 | 5/1997 |
| WO | 1999051642 A1 | 10/1999 |
| WO | 2000000823 A1 | 1/2000 |
| WO | 2000039585 A1 | 7/2000 |
| WO | 2001044516 A2 | 6/2001 |
| WO | 2004009533 A1 | 1/2004 |
| WO | 2004009558 A2 | 1/2004 |
| WO | 2004009610 A2 | 1/2004 |
| WO | 2008101935 A2 | 8/2008 |
| WO | 2011005566 A2 | 1/2011 |
| WO | 2012016930 A1 | 2/2012 |
| WO | 2013142346 A1 | 9/2013 |
| WO | 2014055644 A2 | 4/2014 |
| WO | 2015035091 A1 | 3/2015 |
| WO | 2015109248 A1 | 7/2015 |
| WO | 2015134711 A1 | 9/2015 |
| WO | 2015143441 A1 | 9/2015 |
| WO | 2017015442 A1 | 1/2017 |
| WO | 2017102954 A1 | 6/2017 |
| WO | 2017102955 A1 | 6/2017 |
| WO | 2017102956 A1 | 6/2017 |
| WO | 2018237326 A1 | 12/2018 |

OTHER PUBLICATIONS

Yu et al. TBK1 inhibitors: a review of patent literature (2011-2014), Exp. Opin. Therap. Pat., 25, 1385-1396, 2015. (Year: 2015).*
Jenkins et al. Ex Vivo profiling of immune checkpoint blockade. Cancer Disc. 8, 196-215, 2017. (Year: 2017).*
Lewis et al. "Evidence for the Widespread Coupling of Alternative Splicing and Nonsense-Mediated mRNA Decay in Humans" Jan. 7, 2003, PNAS USA 100(1): 189-192.
Li et al. "Nonsense Surveillance in Lymphocytes?" Feb. 1998, Immunity 8:135-141.
Linde et al. "Introducing Sense into Nonsense in Treatments of Human Genetic Diseases" Nov. 1, 2008, Trends in Genetics 24(11):552-563.
Loudon "Ataluren: a 'no-nonsense' Approach for Pulmonary Diseases" Jun. 2013, Pulmonary Pharmacol. Therap. 26(3):398-399.
Loufrani et al. "Absence of Dystrophin in Mice Reduces NO-dependent Vascular Funcction and Vascular Density: Total Recovery After a Treatment with the Aminoglycoside Gentamicin" Apr. 2004, Arterioscler. Thromb. Vase. Biol. 24(4):671-676.
Makrides "Gene Transfer and Expression in Mamalian Cells" 2003 Ed., Elsvier Sciences B.V., Amsterdam (Title Page and TOC only).
Martin et al. "Identification and Characterization of Small Molecules that Inhibit Nonsense-Mediated RNA Decay and Suppress Nonsense p53 Mutations" Jun. 1, 2014, Cancer Research 74(11):3104-3113.
Martin et al. "The Microtubule-depolymerizing Agent Ansamitocin P3 Programs Dendritic Cells Toward Enhanced Anti-tumor Immunity" Jun. 7, 2014, Cancer Immunology, Immunotherapy, NIH Author Manuscript 63(9):925-938.
McKinney et al. "Structural Insights Lead to a Negamycin Analogue with Improved Antimicrobial Activity Against Gram-Negative Pathogens" Jul. 12, 2015, ACS Med. Chem. Let. 6:930-955.
Mullis et al. "PCR: The Polymerase Chain Reaction" 1994 Ed. Birkhauser (Title Page and TOC only).
Needels et al. "Generation and Screening of an Oligonucleotide-Encoded Synthetic Peptide Library" Nov. 15, 1993 PNAS USA 90(22):10700-10704.
Nguyen et al. "Nonsense-mediated mRNA Decay: Inter-individual Variability and Human Disease" Oct. 1, 2014, Neuroscience and Biobehavioral Reviews 46:175-186.
Pilotte et al. "Reversal of Tumoral Immune Resistance bby Inhibition of Tryptophan 2,3-Dioxygenase" Feb. 14, 2012, PNAS USA 109(7):2497-2502.
Politano et al. "Gentamicin Administration in Duchenne Patients with Premature Stop Codon. Preliminary Results" 2003, Acta Myol. 22:15-21.
Popp et al. "Attenuation of Nonsense-mediated mRNA Decay Facilitates the Response to Chemotherapeutics" Mar. 26, 2015, Nature Communications 6(1) abstract.
Rebibo-Sabbah et al. "In Vitro and Ex Vivo Suppression by Aminoglycosides of PCDH15 Nonsense Mutations and Underlying Type 1 Usher Syndrome" Jul. 25, 2007, Hum. Genet. 122:373-381.
Sambrook et al. "Molecular Cloning: A Laboratory Manual" 2001, 3rd Ed. Cold Spring Harbor Press, Cold Spring Harbor, NY (Title Page and TOC only).
Sambrook et al. "Molecular Cloning: A Laboratory Manual" Fourth Ed, 2012 (TOC and Contents only).
Sausville et al. "Contribution sof Human Tumor Xenografts to Anticancer Drug Development" Apr. 1, 2006, Cancer Research 66(7):3351-3354.
Smith "Vaccinia Virus Vectors for Gene Expression" 1991, Current Opin. Biotechnol. 2:713-717.
Smith et al. "Correction: IDO is a Nodal Pathogenic Drive of Lung Cancer and Metastasis Development" Nov. 26, 2012, Cancer Discov. 2(8):722-735.
Sossi et al. "Premature Termination Mutations in exon 3 of the SMN1 Gene are Associated with Exon Skipping and a Relatively Mild SMA Phenotype" 2001, Eur. J. Hum. Genet. 9:113-120.
Supplementary European Search Report and Written Opinion for EP 16880163 dated Sep. 30, 2019.
Supplementary European Search Report and Written Opinion for EP 16880164 dated Oct. 1, 2019.
Supplementary European Search Report and Written Opinion for EP 16880165 dated Sep. 30, 2019.
Tomoka et al. "Rigosertib Induces Cell Death of a Myelodysplastic Syndrome-derived Cell Line by DNA Damage-induced G2/M Arrest" Mar. 2015, Cancer Science 106(3):287-293.
Usuki et al. "Inhibition of SMG-8, a Subunit of SMG-1 Kinase, Ameliorates Nonsense-mediated mRNA Decay-exacerbated Mutant Phenotypes Without Cytotoxicity" Aug. 27, 2013, PNAS 110(37): 15037-15042.
Weinmann "Cancer Immunotherapy: Selected Targets and Small-Molecule Modulators" Feb. 2, 2016, ChemMedChem. 11(5):450-466.
Xiao-Dong et al. "Pivotal Roles of cGAS-cGAMP Signaling in Antiviral Defense and Immune Adjuvant Effects" Sep. 20, 2013, Science 341(6152)a;1390-1394.
Zhan et al. "From Monoclonal Antibodies to Small Molecules: The Development of Inhibitors Targeting the PD-1/PD-L1 Pathway" Jun. 2016, Drug Disc. Today 21(6):1027-1036.
Zilberberg et al. "Restoration of APC Gene Function in Colorectal Cancer Cells by Aminoglycoside- and Macroline-induced Reatthrough of Premature Termination Codons" Dec. 1, 2009, GUT 59(4):496-507.
Piekarz et al. "Epigenetic Modifiers: Basic Understanding and Clinical Development" Jun. 2009, Clinical Cancer Research 15(12):3918-3926.

(56) References Cited

OTHER PUBLICATIONS

Adams et al. "Big Opportunities for Small Molecules in Immuno-Oncology" Sep. 2015, Nature Rev. Drug. Disc. 14:603-622.
Ausubel et al. "Current Protocols in Molecular Biology" 1987 Ed. John Wiley & Sons, Inc., New York, NY (Title Page and TOC only).
Beaucage et al. Current Protocols in Nucleic Acid Chemistry, 2000 Ed. John Wiley & Sons, Inc., New York, NY (Title Page and TOC only).
Behm-Ansmant et al. "Quality Control of Gene Expression: a Stepwise Assembly Pathway for the Surveillance Complex that Triggers Nonsense-mediated mRNA Decay" Feb. 15, 2006, Genes & Development 20(4):391-398.
Bidou et al. "Sense from Nonsense: Therapies for Premature Stop Codon Diseases" Nov. 1, 2012, Molecular Medicine Today 18(11):679-688.
Bidou et al. "Sense from Nonsense: Therapies for Premature Stop Codon Diseases" Nov. 2012, Trends Molec. Med. 18(11):679-688.
Bordeira-Carrico et al. "Cancer Syndromes and Therapy by Stop-Codon Readthrough" Nov. 2012, Trends in Molecular Medicine 18(11):667-678.
Buck et al. "Stop Codon Read-through of a Methylamalonic Aciduria Mutation" Aug. 1, 2009, Molecular Genetics and Metabolism Academic Press 97(4):244-249.
Chakradhar et al. "Bringing RNA Into the Fold: Small Molecules Find New Targets in RNA to Combat Disease" May 2017, Nature Medicine 23(5):532-534.
Clackson et al. "Making Antibody Fragments Using Phase Display Libraries" Aug. 15, 1991, Nature 352:624-628.
Culbertson "RNA Surveillance: Unforeseen Consequences for Gene Expression, Inherited Genetic Disorders and Cancer" Feb. 1, 1999, Trends in Genetics 15(2):74-80.
Curran et al. "PD-1 and CTLA-4 Combination Blockade Expands Infiltrating T Cells and Reduces Regulatory T and Myeloid Cells Within B16 Melanoma Tumors" Mar. 2, 2010, PNAS USA 107(9):4275-4280.
Derosa et al. "Alternative Splicing and Nonsense-mediated mRNA Decay in the Regulation of a New Adenomatous Polyposis Coli Transcript" May 5, 2007, Gene 395(1-2):8-14.
Diner et al. "The Innate Immune DNA Sensor cGAS Produces a Noncanonical Cyclic Dinucleotide that Activates Human STING" May 30, 2013, Cell Rep. 3(5):1355-1361.
Du et al. "A New Series of Small Molecular Weight Compounds Induce Read Through of All Three Types of Nonsense Mutations in the ATM Gene" Sep. 1, 2013, Molecular Therapy 21(9):1653-1660.
Du et al. "Aminoglycoside Suppression of a Premature Stop Mutation in a Cftr-/-mouse Carrying a human CFTR-G542X Transgene" Jul. 3, 2002, J. Mol. Med. 80:595-604.
Du et al. "Nonaminoglycoside Compounds Induce Readthrough of Nonsense Mutations" Sep. 21, 2009, J. Exp. Med. 206(10):2285-2297.
Duncan et al. "The Binding Site for C1q on IgG" Apr. 21, 1988, Nature 332:738-740.
Duraiswamy et al. "Dual Blockade of PD-1 and CTLA-4 Combined with Tumor Vaccine Effectively Restores T-Cell Rejection Function in Tumors" 2013, Cancer Research 73(12):3591-3603.
Duraiswamy et al. "Therapeutic PD-1 Pathway Blockade Augments with Other Modalities of Immunotherapy 5"Cell Function to Prevent Immune Decline in Ovarian Cancer" Dec. 1, 2013, Cancer Research 73(23):6900-6912.
Durand et al. "Inihibition of Nonsense-mediated mRNA Decay (NMD) by a New Chemical Molecule Reveals the Dynamic of NMD Factors in P-bodies" Sep. 24, 2007 J. Cell Biology 178(7):1145-1160.
Fernando et al. "Induction of Tumour Immunity by Targeted Inhibition of Nonsense-mediated mRNA Decay" May 13, 2010, Nature 465(7295):227-230.
Floquet et al. "Readthrough of Premature Termination Codons in the Adenomatous Polyposis Coli Gene Restores Its Biological Activity in Human Cancer Cells" Aug. 31, 2011, PLOS ONE 6(8):e24125.

Floquet et al. "Rescue of Non-sense Mutated p53 Tumor Suppressor Gene by Aminoglycosides" Apr. 1, 2011, Nucleic Acids Research 39(8):3350-3362.
Geysen et al. "Small Peptides Induce Antibodies with a Sequence and Structural Requirement for Binding Antigen Comparable to Antibodies Raised Against the Native Protein" Jan. 1, 1985, PNAS USA 82(1):178-182.
Geysen et al. "Strategies for Epitope Analysis Using Peptide Synthesis" Sep. 24, 1987, J. Immunol. Meth. 102(2):259-274.
Geysen et al. "Use of Peptide Synthesis to Probe Viral Antigens for Epitopes to a Resolution of a Single Amino Acid" Jul. 1, 1984, PNAS USA 81(13):3998-4002.
Gilboa et al. "Reducing Toxicity of Immune Therapy Using Aptamer-Targeted Drug Delivery" 2105, Cancer Immunol. Res. 3(11);1195-1200.
Gray et al. "Combination of HDAC and Topoisomerase Inhibitors in Small Cell Lung Cancer" Jun. 2012, Cancer Biology & Therapy 13(8):614-622.
Greenfield "Antibodies: A Laboratory Manual"2014, 2nd Ed., Cold Spring Harbor Press, Cold Spring Harbor, NY (Title Page and TOC only).
Helip-Wooley et al. "Expression of CTNS Alleles: Subcellular Localization and Aminoglycoside Correction in Vitro" Feb. 2002, Mol. Genet. Metab. 75(2):128-133.
Hentze et al. "A Perfect Message: RNA Surveillance and Nonsense-Mediated Decay" Feb. 5, 1999, Cell 96:307-310.
Hirawat et al. "Safety, Tolerability, and Pharmacokinetics of PTC124, a Nonaminoglycoside Nonsense Mutation Suppressor, Following Single- and Multiple-Dose Administration to Healthy Male and Female Adult Volunteers" 2007, J. Cliin. Pharmacol. 47:430-444.
Holtmeier et al. "?? T Cells Link Innate and Adaptive Immune Responsses" 2005, Chemical Immunology and Allergy 86:151-183.
Horgan et al. "Current Protocols in Immunology" 1994, John Wiley & Sons, Inc., New York, NY (Title Page and TOC only).
Ino et al. "Role of the Immune Tolerance-Inducing Molecule Indoleamine 2,3-Dioxygenase in Gynecological Cancers" 2012, J. Cancer Sci. Ther. S13:001.
International Search Report and Written Opinion for PCT/US2016/068588 dated Mar. 31, 2017.
International Search Report and Written Opinion for PCT/US2016/068589 dated Mar. 31, 2017.
International Search Report and Written Opinion for PCT/US2016/068591 dated Mar. 29, 2017.
International Search Report and Written Opinion for PCT/US2018/039102 dated Sep. 27, 2018.
Ishikawa et al. "STING Regulates Intracellular DNA-Mediated, Type I Interferon-Dependent Innate Immunity" Oct. 8, 2009, Nature 461:788-792.
Jamila et al. "Nonsense-mediated mRNA Decay Impacts MSI-driven Carcinogenesis and Anti-Tumor Immunity in Colorectal Cancers" Jul. 9, 2008, PLOS ONE 3(7):e2583.
Johnson et al. "Relationships Between Drug Activity in NCI Preclinical in vitro and in vivo Models and Early Clinical Trials" 2001, Br. J. Cancer 84(10):1424-1431.
Kang et al. "Evidence for Non-V3-Specific Neutralizing Antibodies that Interfere with gp120/CD4 Binding in Human Immunodeficiency Virus 1-infected Humans" Jul. 15, 1991, PNAS USA 88(14):6171-6175.
Kayali et al. "Read-Through Compound 13 Restores Dystrophin Expression and Improves Muscle Function in the mdx Mouse Model for Duchenne Musxcular Dystrophy" Sep. 15, 2012, Hum. Mol. Gen. 21(18)-4007-4020.
Keeling et al. "Clinically relevant aminoglycosides Can Suppress Disease-Associated Premature Stop Mutations in the IDUA and P53 cDNAs in a Mammalian Translation System" Jun. 1, 2002, J. Molecular Med. 80(6):367-376.
Keeling et al. "Gentamicin-mediated Suppression of Hurler Syndrome Stop Mutations Restores a Low Level of ?-L-iduronidase Activity and Reduces Lysosomal Glycosaminoglycan Accumulation" Feb. 1, 2001, Hum. Mol. Genet. 10(3):291-299.

(56) References Cited

OTHER PUBLICATIONS

Lai et al. "Correction of ATM Gene Function by Aminoglycoside-Induced Read-Through of Premature Termination Codons" Nov. 2, 2004, PNAS USA 101(44):15676-15681.

Lavin "Generating SM(a)RTer Compounds for Translation Termination Suppression in A-T and Other Genetic Disorders" Sep. 1, 2013, Molecular Therapy 21(9):1651-1652.

Lee et al. "Pharmaceutical Therapies to Recode Nonsense Mutations in Inherited Diseases" 2012, Pharmacol. & Therap. 136:227-266.

Harvey et al., Lippinocott's Illustrated Reviews: Pharmacology, 2nd edition, 1997, Chapter 38, p. 373.

Challa et al. "IKBKE is a Substrate of EGFR and a Therapeutic Target in Non-Small Cell Lung Cancer with Activating Mutations of EGFR" Jun. 10, 2016, Cancer Res. 76(15):44 18-4429.

Emens et al. "Cancer Immunotherapy: Opportunities and Challenges in the Rapidly Evolving Clinical Landscape" Jun. 15, 2017, Eur. J. Cancer 81:116-129.

Hasan et al. "Therapeutic Potential of Targeting TBK1 in Autoimmune Diseases and Interferonopathies" Jun. 25, 2016, Pharmacol. Res. 111:336-342.

Jenkins et al. "Ex Vivo Profiling of PD-1 Blockade Using Organotypic Tumor Spheroids" Nov. 3, 2017, Cancer Discovery 8(2):196-215.

Pastor et al. "Induction of Tumour Immunity by Targeted Inhibition of Nonsense-mediated mRNA Decay" May 13, 2010, Nature 465(7295):227-230.

Extended European Search Report for EP 18821002.5 dated Feb. 17, 2021.

Xiao et al. "The Kinase TBK1 Functions in Dendritic Cells to Regulate T Cell Homeostasis, Autoimmunity and Antitumor Immunity" Mar. 29, 2017, J Exper. Medicine 214(5):1493-1507.

Zhu et al. "TBKBP1 and TBK1 Form a Growth Factor Signalling Axis Mediating Immunosuppression and Tumourigenesis" Dec. 1, 2019, Nature Cell Biology 21(12):1604-1614.

Riaz et al., "The Role of Neoantigens in Response to Immune Checkpoint Blockade," International Immunology, vol. 28, No. 8, pp. 411-419.

\* cited by examiner

METHODS FOR TREATING COLON CANCER WITH COMPOSITIONS COMPRISING AMLEXANOX AND IMMUNE CHECKPOINT INHIBITORS

CLAIM OF PRIORITY

This application is a U.S. national stage filing under 35 U.S.C. § 371 of International Application No. PCT/US2018/039102 filed on Jun. 22, 2018 which claims priority to U.S. Provisional Application No. 62/523,537 filed Jun. 22, 2017, titled "METHODS FOR TREATING CANCER WITH COMPOSITIONS COMPRISING AMLEXANOX AND IMMUNE MODULATORS," and each of these applications is incorporated herein by reference.

SUMMARY

Disclosed herein are compositions and methods for treating cancer in a subject. In some embodiments, the methods involve generating an immune response in an individual by inducing the expression of neoantigens on the surface of abnormal (such as proliferative) cells. This can be achieved by promoting premature termination codon (PTC) read-through in an mRNA and/or inhibiting nonsense-mediated decay (NMD) of an mRNA.

In one embodiment, a method of treating a subject with cancer may comprise administering a therapeutically effective amount of a compound that both promotes premature termination codon (PTC) read-through in an mRNA and inhibits the nonsense-mediated decay (NMD) of an mRNA. In some embodiments, the compound is amlexanox. In some embodiments, the method further comprises administering molecules that inhibit immune checkpoint proteins.

In one embodiment, a method of treating cancer in a subject comprises administering amlexanox in combination with immune modulators, such as checkpoint inhibitors, immune co-stimulatory molecules, TLR agonists, TNFR superfamily agonists, cyclic dinucleotides, T-cell agonists, cytokines, chemokines, and oncolytic virus.

In one embodiment, a method of treating cancer in a subject comprises administering amlexanox in combination with molecules that inhibit at least one immune checkpoint protein disclosed herein. In one embodiment, the checkpoint protein is selected from PD-1, PD-L1, and CTLA-4. In some embodiments, the method comprises administering amlexanox in combination with anti-PD-1 antibodies. In some embodiments, the method comprises administering amlexanox in combination with anti-PD-L1 antibodies. In some embodiments, the method comprises administering amlexanox in combination with anti-CTLA-4 antibodies. In some embodiments, the method comprises administering amlexanox in combination with anti-PD-1 and anti-CTLA-4 antibodies. In some embodiments, the method comprises administering amlexanox in combination with anti-PD-L1 and anti-CTLA-4 antibodies.

In another embodiment, a method of killing cancer cells may comprise contacting the cancer cells with a composition comprising amlexanox in combination with molecules that inhibit at least one immune checkpoint protein. In some embodiments, the method may be in vitro or in vivo.

In an additional embodiment, a method of killing cancer stem cells may comprise contacting the cancer stem cells with a composition comprising amlexanox in combination with molecules that inhibit at least one immune checkpoint protein. In some embodiments, the method may be in vitro or in vivo.

In a further embodiment, a method for inducing the expression of one or more neoantigens on the surface of an abnormal cell comprises contacting the abnormal cell with amlexanox in combination with molecules that inhibit at least one immune checkpoint protein. In some embodiments, the method may be in vitro or in vivo.

In another embodiment, a method for generating an immune response in an individual in need thereof comprising administering to the individual a therapeutically effective amount of a compound that both promotes premature termination codon (PTC) read-through in an mRNA and inhibits the nonsense-mediated decay (NMD) of an mRNA. In some embodiments, the compound is amlexanox. In some embodiments, the method further comprises administering molecules that inhibit immune checkpoint proteins. In some embodiments, the checkpoint proteins are PD-1, PD-L1, and CTLA-4.

DETAILED DESCRIPTION

Figure 1:
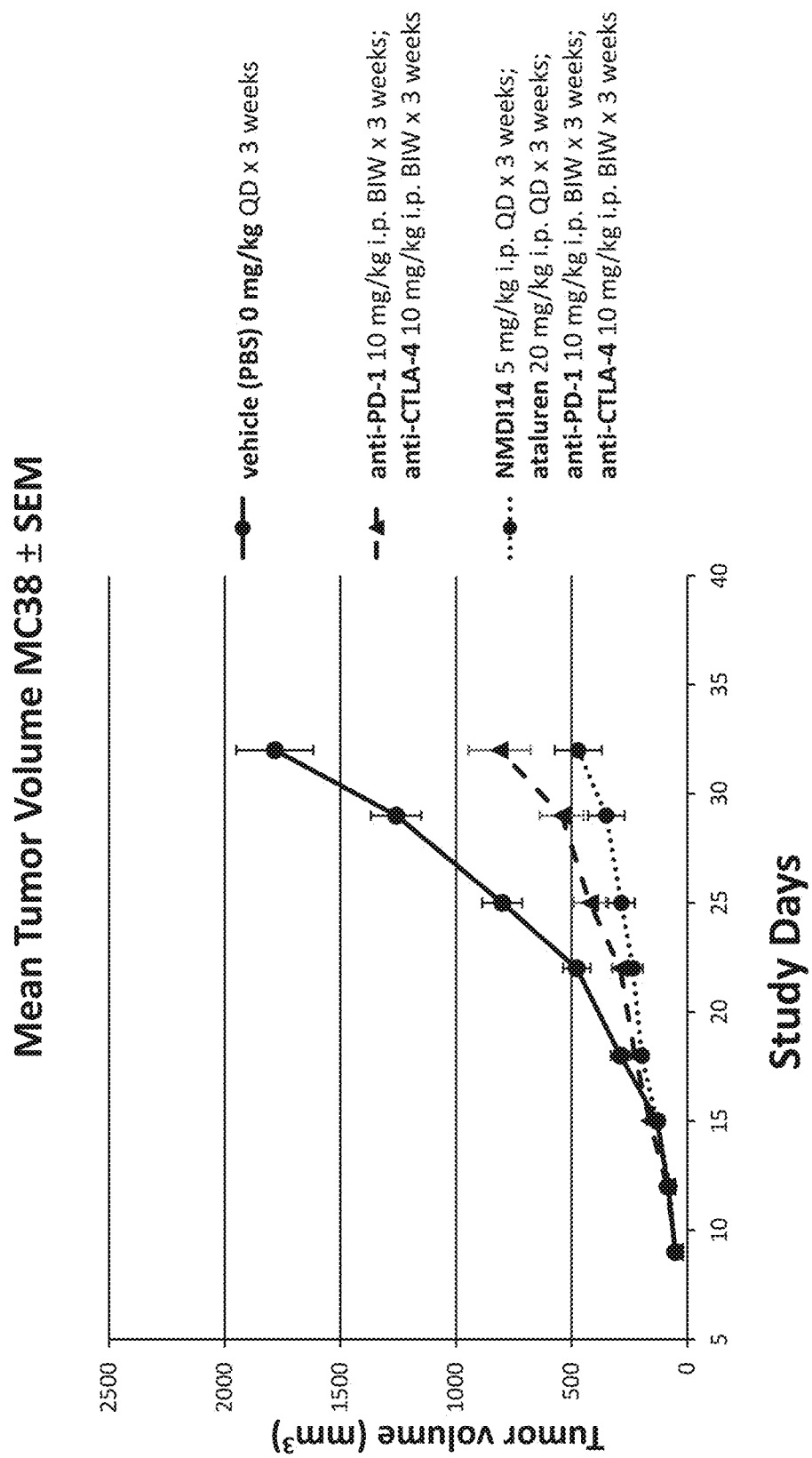
FIG. 1 depicts a graph comparing the effect of administration of PTC124 (Ataluren) and NMDI14 in combination with anti-PD-1 antibody and anti-CTLA-4 antibody on tumor volume (mm3).

A major impediment to the efficacy of checkpoint blockade for cancer immunotherapy relates to the scarcity of potent tumor neoantigens expressed by late stage cancers that have undergone extensive immunoediting. This process takes place early in the lifecycle of a tumor, and results in the deletion of populations of tumor cells that expressed immunogenic or strong tumor specific antigens and were therefore targeted by cytotoxic T cells. A mature tumor, therefore, is comprised mainly of tumor cells that have evolved multiple immunoevasion strategies, such as expression of only weak tumor antigens, and are therefore less likely to be effectively targeted by cytotoxic T cells. Despite the recent successes of checkpoint blockade as an immunotherapeutic modality in cancer, the efficacy of these drugs is highly correlated with the availability of robust tumor neoantigens. Notably, tumors in which these drugs are most effective are those with the highest mutational load, such as melanoma and non-small cell lung cancer (NSCLC), both of which carry strong environmentally-induced mutational signatures of UV damage and smoking, respectively.

Accordingly, disclosed herein are methods and compositions for generating an immune response in an individual having cells that express one or more messenger RNA (mRNA) molecules bearing a premature termination codon (PTC), by inducing the expression of one or more neoantigens on the surface of those cells. The method is based, in part, that inhibition of molecular pathways associated with the regulation of nonsense mediated decay (NMD) results in the "read-through" and subsequent translation of mRNAs bearing PTCs into polypeptides having amino acid sequences that vary from the corresponding wild type protein, sometime significantly. Without being bound to theory, proteolysis and presentation of these peptides on the surface of cells via major histocompatibility complex (MHC) molecules can result in a highly antigenic target for attack by components of the immune system, for example, T cells. As will be described further below, not only does a combination of compounds that promote PTC read-through and inhibit NMD effectively inhibit the replication of tumor cells in an in vivo model, the addition of compounds specific for one or more immune checkpoint molecules to the treatment regimen synergistically enhances the anti-proliferative effect. Thus, methods disclosed herein have particular utility for the treatment of diseases characterized by hyperproliferative cells, such as, for example, cancer due to the hypermutable nature of rapidly dividing cells. Cancer cells avoid detection by the immune system in part by displaying only weakly- or non-antigenic peptides on their surface. Accordingly, the compositions and methods disclosed herein provide an effective way to induce the expression of neoantigens on the surface of cancer cells, thereby rendering them vulnerable to attack by the immune system.

Efforts in tumor vaccine development in parallel with advances in immunotherapy have led to current approaches in which RNAseq/exome sequencing performed on tumor samples identifies mutated transcripts which are then selected for their ability to serve as robust neoantigens, and are then used as the basis for vaccine development. By virtue of the nature of these mutation detection methods, the overwhelming majority of mRNA species detected are those that contain missense mutations in the coding sequencing, generated by nucleotide transitions and transversions, which lead to either silent or single amino acid substitutions. Although these proteins have the ability to serve as neoantigens, it would be far preferable to identify mutant mRNA species that have more than one amino acid difference, which could then serve as far more robust neoantigens.

A more desirable pool of tumor mRNAs from which to derive robust tumor neoantigens would be those containing premature termination codons (PTC). These mRNA species contain much more deleterious mutations such as insertions, deletions, nonsense mutations and nonstop (delayed termination) mutations. Paradoxically, however, these same PTC-containing species are highly unstable and are rapidly degraded by the nonsense-mediated decay (NMD) pathway, therefore they are generally undetectable in RNA sequencing due to their very low abundance or complete absence, and are rarely if ever translated into protein. PTC-containing mRNAs have the potential to encode many divergent amino acids from the wild type sequence due to the shift in reading frame and/or usage of alternate termination codons. If proteins could be transcribed from PTC-containing mRNA species, they would represent a source of extraordinarily potent tumor neoantigens since they can encode proteins with vastly divergent sequences. A therapeutic approach aimed at blocking the NMD pathway and promoting PTC read-through in tumors would allow PTC-containing transcripts to be translated, and strong neoantigens to be expressed in vivo.

Premature termination codon (PTC) mutations are those in which a base substitution or frameshift mutation changes a sense codon into one of three stop codons (UAA, UAG, or UGA). Studies of yeast, human genetic disorders, and immunoglobulin family gene expression have identified an RNA surveillance mechanism that minimizes the translation and regulates the RNA stability of nonsense RNAs containing such chain termination mutations. This surveillance mechanism is called "nonsense-mediated mRNA decay" ("NMD)". NMD is a post transcriptional mechanism that is operational in both normal cells (e.g., B and T cells) and cells with genetic mutations (i.e., cells with mutations in genes controlling cellular proliferation).

While many of the proteins involved in NMD are not conserved between species, in *Saccharomyces cerevisiae* (yeast), there are three main factors in NMD: UPF1, UPF2 and UPF3 (UPF3A and UPF3B in humans), that make up the conserved core of the NMD pathway. All three of these factors are trans-acting elements called up-frameshift (UPF) proteins. In mammals, UPF2 and UPF3 are part of the "exon-exon junction complex" (EJC) bound to mRNA after splicing along with other proteins which also function in NMD. UPF1 phosphorylation is controlled by the proteins SMG-1, SMG-5, SMG-6 and SMG-7.

The process of detecting aberrant transcripts occurs during translation of the mRNA. A popular model for the detection of aberrant transcripts in mammals suggests that during the first round of translation, the ribosome removes the exon-exon junction complexes bound to the mRNA after splicing occurs. If after this first round of translation, any of these proteins remain bound to the mRNA, NMD is activated. Exon-exon junction complexes located downstream of a PTC are not removed from the transcript because the ribosome is released before reaching them. Termination of translation leads to the assembly of a complex composed of UPF1, SMG1 and the release factors, eRF1 and eRF2, on the mRNA. If an EJC is left on the mRNA because the transcript contains a PTC, then UPF1 comes into contact with UPF2 and UPF3, triggering the phosphorylation of UPF1.

In vertebrates, the location of the last exon-junction complex relative to the termination codon usually determines whether the transcript will be subjected to NMD or not. If the termination codon is downstream of or within about 50 nucleotides of the final exon-junction complex then the transcript is translated normally. However, if the termination codon is further than about 50 nucleotides upstream of any exon-junction complexes, then the transcript is down regulated by NMD. The phosphorylated UPF1 then interacts with SMG-5, SMG-6 and SMG-7, which promote the dephosphorylation of UPF1. SMG-7 is thought to be the terminating effector in NMD, as it accumulates in P-bodies, which are cytoplasmic sites for mRNA decay. In both yeast and human cells, the major pathway for mRNA decay is initiated by the removal of the 5' cap followed by degradation by XRN1, an exoribonuclease enzyme. The other pathway by which mRNA is degraded is by deadenylation from 3'-5'.

Accordingly, without being bound to theory, there are at least two ways to evade the NMD pathway in order to induce the translation of an mRNA bearing a PTC into a polypeptide: 1) provide a compound that promotes read-through of a PTC, thus ensuring the removal of all EJCs associated with mRNA during the initial round of translation by the ribosome; and/or 2) inhibition of one or more proteins associated with the NMD degradation complex (such as, but not limited to, UPF1, UPF2, UPF3, eIF4AIII, MLN51, the Y14/MAGOH heterodimer, SMG-1, SMG-5, SMG-6 and/or SMG-7).

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art.

Nothing herein is to be construed as an admission that the invention is not entitled to antedate such disclosure by virtue of prior invention.

As used herein, a "premature termination codon" (PTC) or "premature stop codon" refers to the introduction of a stop codon into an mRNA (prior to the endogenous termination codon) as the result of a mutation.

A "nonsense mutation," as used herein, is a point mutation in a sequence of DNA resulting in a PTC, or a nonsense codon, in the transcribed mRNA, and in a truncated, incomplete, and usually nonfunctional protein product. Nonsense mutations are genetic mutations that may underlie a variety of diseases, particularly those that are genetically inherited. In cancer, for example, nonsense mutations are generally acquired or somatic mutations in the tumor. In some embodiments, the nonsense mutation is a somatic mutation. In another embodiment, the nonsense mutation is not a germline mutation.

A "nonstop mutation" is a point mutation in the endogenous termination codon that leads to continued and inappropriate translation of the mRNA into the 3' untranslated region. A nonstop mutation leads to incorporation of an abnormal amino acid sequence and utilization of a downstream termination codon. In some embodiments, the nonstop mutation is a somatic mutation. In another embodiment, the nonstop mutation is not a germline mutation.

A "frameshift mutation" refers to a deletion or insertion of one or more nucleotides within an open reading frame, for example, a single nucleotide or dinucleotide deletion or insertion, such that the reading frame of the coding region is shifted by one or two nucleotides. Thus, the amino acid sequence of a polypeptide translated from an mRNA bearing a frameshift mutation is highly dissimilar to the corresponding wild type sequence. In some embodiments, a frameshift mutation produces a PTC. In some embodiments, the frameshift mutation is a nucleotide or dinucleotide deletion leading to a +1 or +2 frameshift mutation. However, any number of nucleotide deletions can occur provided a frameshift mutation results. Alternatively, the insertion of one or more nucleotides may give rise to a frameshift and such mutations also form part of the present invention. Other genetic modifications which give rise to a frameshift also form part of the present invention, such as a splice site mutation that results in exon skipping or retention of an intronic sequence or change in the nucleotide sequence which leads to translation initiation from a different position or a mutation outside a coding region, such as within an intron or a 5' or 3' untranslated region, which mutation may result in mistranslation and production of a mutant protein. In this type of gene mutation, the mutant protein would be completely mutant amino acid sequences and would contain no wild-type sequences. In some embodiments, a frameshift mutation can lead to a premature termination codon (when it occurs early in the mRNA) or alternatively a delayed termination codon (when it occurs near to the endogenous termination codon. In some embodiments, the frameshift mutation is a somatic mutation. In another embodiment, the frameshift mutation is not a germline mutation.

A "nonfunctional" polypeptide, as used herein, refers to a polypeptide that, due to one or more mutations, is unable to perform a function in a cellular context in comparison to a corresponding non-mutated (wild type) polypeptide. A "functional" polypeptide is a polypeptide that can, at least to some extent, perform a cellular function even though it may have one or more mutated amino acids in comparison to a corresponding non-mutated (wild type) polypeptide.

The term "read-through" herein means to skip over a premature termination codon in ribosomal translation, or to substitute an amino acid, or to suppress degradation of mRNA that comprises a premature termination codon.

As used herein, the term "polypeptides" includes proteins, peptides, fragments of polypeptides, and fusion polypeptides.

The term "animal," "patient," or "subject" as used herein includes, but is not limited to, humans and non-human vertebrates such as wild, domestic and farm animals. Preferably, the term refers to humans. The terms "subject", "patient" or "individual" are used interchangeably herein, and refers to a mammalian subject to be treated. In some embodiments, the patient is a human. In some cases, the methods can be used in experimental animals, in veterinary application, and in the development of animal models for disease, including, but not limited to, rodents including mice, rats, and hamsters; and primates. In some embodiments, the patient is a patient in need thereof.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

Unless defined otherwise herein, all technical and scientific terms used herein have the same meaning as commonly understood by one of ordinary skill in the art to which this invention pertains.

As used herein and in the appended claims, the singular forms "a", "an", and "the" include plural reference unless the context clearly dictates otherwise. Thus, for example, reference to an "antioxidant" is a reference to one or more antioxidants and equivalents thereof known to those skilled in the art, and so forth.

"Administering" when used in conjunction with a therapeutic means to administer a therapeutic to a patient whereby the therapeutic positively impacts the tissue to which it is targeted. The compounds described herein can be administered either alone or in combination (concurrently or serially) with other pharmaceuticals. For example, the compounds can be administered in combination with other anti-cancer or anti-neoplastic agents, or in combination with other cancer therapies other than chemotherapy, such as, for example, surgery or radiotherapy. In some embodiments, the compounds described herein can also be administered in combination with (i.e., as a combined formulation or as separate formulations) other therapeutics.

A "therapeutically effective amount" or "effective amount" of a composition is a predetermined amount calculated to achieve the desired effect, i.e., to ameliorate, prevent or improve an unwanted condition, disease or symptom of a patient. The activity contemplated by the present methods may include both therapeutic and/or prophylactic treatment, as appropriate. The specific dose of the compounds administered according to this invention to obtain therapeutic and/or prophylactic effects will, of course, be determined by the particular circumstances surrounding the case, including, for example, the compounds administered, the route of administration, and the condition being treated. The effective amount administered may be determined by a physician in the light of the relevant circumstances including the condition to be treated, the choice of compounds to be administered, and the chosen route of administration. A therapeutically effective amount of the compound of this invention is typically an amount such that when it is administered in a physiologically tolerable excipient composition, it is sufficient to achieve an effective systemic concentration or local concentration in the target tissue.

As used herein, the term "therapeutic" means an agent utilized to discourage, combat, ameliorate, prevent or improve an unwanted condition, disease or symptom of a patient.

By "pharmaceutically acceptable", it is meant the carrier, diluent or excipient must be compatible with the other ingredients of the formulation and not deleterious to the recipient thereof.

By the term "modulate," it is meant that any of the mentioned activities, are, e.g., increased, enhanced, increased, agonized (acts as an agonist), or promoted. Modulation can increase activity more than 1-fold, 2-fold, 3-fold, 5-fold, 10-fold, 100-fold, etc., over baseline values. Modulation can also decrease its activity below baseline values, and act as an antagonist or an inhibitor. Modulation can also normalize an activity to a baseline value.

The term "Immune Modulators" includes, without limitation, checkpoint inhibitors, immune co-stimulatory molecules, TLR agonists, TNFR superfamily agonists, cyclic dinucleotides, T-cell agonists, cytokines, chemokines, oncolytic virus, and any other agents that stimulate or inhibit immune response.

As used herein, the phrase "in need thereof" means that the patient has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

"Treatment" is an intervention performed with the intention of preventing the development or altering the pathology or symptoms of a disorder. Accordingly, "treatment" can refer to therapeutic treatment or prophylactic or preventative measures. In some embodiments, the treatment is for therapeutic treatment. In some embodiments, the treatment is for prophylactic or preventative treatment. Those in need of treatment can include those already with the disorder as well as those in which the disorder is to be prevented.

As used herein, the phrase "treating cancer" refers to inhibition of cancer cell replication, apoptosis, inhibition of cancer spread (metastasis), inhibition of tumor growth, reduction of cancer cell number or tumor growth, decrease in the malignant grade of a cancer (e.g., increased differentiation), or improved cancer-related symptoms.

As used herein, the term "alkyl" means a saturated hydrocarbon group which is straight-chained or branched. Alkyl may be heteroalkyl.

As used herein, the term "substituted alkyl" refers to an alkyl as just described in which one or more hydrogen atoms attached to carbon of the alkyl is replaced by another group.

As used herein, the term "heteroalkyl" refers to alkyl groups in which one or more C atoms are replaced by oxygen, nitrogen, sulfur or combinations thereof.

As used herein, the term "alkenyl" means a straight or branched alkyl group having one or more double carbon-carbon bonds. Alkenyl may be heteroalkenyl.

As used herein, the term "substituted alkenyl" refers to an alkenyl as just described in which one or more hydrogen atoms attached to carbon of the alkenyl is replaced by another group.

As used herein, the term "heteroalkenyl" refers to alkenyl groups in which one or more C atoms are replaced by oxygen, nitrogen, sulfur or combinations thereof.

As used herein, the term "alkynyl" means a straight or branched alkyl group having one or more triple carbon-carbon bonds. Alkynyl may be heteroalkynyl.

As used herein, the term "substituted alkynyl" refers to an alkynyl as just described in which one or more hydrogen atoms attached to carbon of the alkynyl is replaced by another group.

As used herein, the term "heteroalkynyl" refers to alkynyl groups in which one or more C atoms are replaced by oxygen, nitrogen, sulfur or combinations thereof.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, biphenyl, benzyl, naphthyl, anthracenyl, phenanthrenyl, indanyl, indenyl, tetrahydronaphthyl, and the like. Aryl may be heteroaryl.

As used herein, the term "substituted aryl" refers to aryl as just described in which one or more hydrogen atoms attached to any carbon atoms is replaced by one or more functional groups.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen.

As used herein, the term "arylalkyl" means a C1-6 alkyl substituted by aryl.

As used herein, the term "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring.

Disclosed herein are methods to treat a subject with cancer. In some embodiments, a method of treating a subject with cancer may comprise administering a therapeutically effective amount of a compound that both promotes premature termination codon (PTC) read-through in an mRNA and inhibits the nonsense-mediated decay (NMD) of an mRNA. In some embodiments, the compound that has both these properties is amlexanox.

In some embodiments, a method of treating a subject with cancer may include administering a therapeutically effective amount of amlexanox compound.

In some embodiments, amlexanox ((2-amino-7-isopropyl-5-oxo-5H-chromeno[2,3-b]pyridine-3-carboxylic acid) is represented by Formula I as follows:

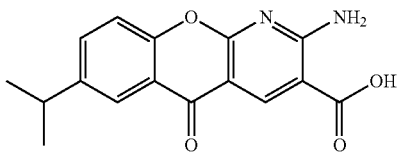

or a salt, solvate, clathrate, hydrate or polymorph thereof.

In some embodiments, amlexanox or its homologues can be represented by Formula II:

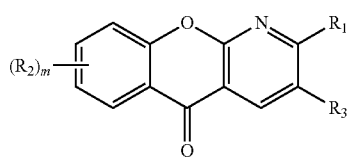

wherein R1 is hydrogen, alkyl, phenyl, carboxyl, hydroxyl, alkoxyl, carboxyalkyl such as esters, cyano, acylamino, or amino which may be unsubstituted or substituted by up to two alkyl groups;

m is 0, 1, or 2;

R2 is alkyl, alkenyl, alkoxy, halogen, nitro, hydroxy, carboxyl, butadienylene (—CH═CH—CH═CH—) which forms a benzene ring with any adjacent carbon atoms, cyano, carboxyalkyl, trifluoromethyl, or amino which may be unsubstituted or substituted by at least one alkyl group; and R3 is carboxyl, cyano, arylalkoxycarbonyl, alkoxycarbonyl, or carboxamide, which may be unsubstituted or substituted by at least one alkyl group, and the salts thereof, In some embodiments, amlexanox may be deuterated amlexanox represented by Formula III as follows:

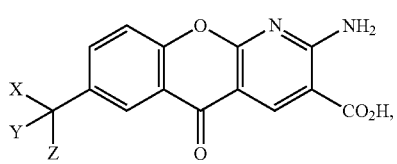

or a pharmaceutically acceptable salt thereof, wherein X, Y, or Z is a group that comprises deuterium (D). In some embodiments, X is a group that comprises D; in some embodiments, X and Y are groups that comprise D; and in some embodiments X, Y, and Z are groups that comprise D. In some embodiments, X, Y, or Z comprises or is CD3; in some embodiments, X, Y, or Z comprises or is D; in some embodiments, X, Y, or Z comprises or is CH2CDH2; in some embodiments, X and Y comprise or are CD3 and Z comprises or is D; in some embodiments, X and Y comprise or are CH3 and Z comprises or is D; and in some embodiments, X comprises or is CH3, Y comprises or is CH2D, and Z comprises or is D.

In some embodiments, amlexanox is administered to a subject having cancer selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia, chronic leukemia; polycythemia vera, lymphoma, multiple myeloma, Waldenstrom's macroglobulinemia, and heavy chain disease. In some embodiments, administration of amlexanox will induce the expression of neoantigens in these cancers thereby eliciting an immune response in the subject.

Without wishing to be bound by theory, it is believed that cancers that exhibit high frequency of nonsense mutations will be more sensitive to amlexanox, inhibitors of NMD complex, and other agents disclosed herein. Such cancers include, but not limited to uterine corpus endometrioid carcinoma (UCEC), bladder urothelial carcinoma (BLCA), stomach cancer, head and neck cancer, kidney renal cell carcinoma, colon adenocarcinoma, esophageal carcinoma, lung squamous cell carcinoma, rectum adenocarcinoma, pancreas adenocarcinoma, lung adenocarcinoma, skin cutaneous melanoma, liver hepatocellular carcinoma, and the like. Such cancers may have higher remission rates when treated with amlexanox or other NMD complex inhibitors, and when compared to a standard chemotherapy regime. In some embodiments, these nonsense mutations are not present in tumor suppressor genes. In some embodiments, administration of amlexanox will induce the expression of neoantigens in these cancers thereby eliciting an immune response in the subject.

In some embodiments, the method of treating cancer in a subject includes administering amlexanox in combination with compounds that promote PTC read-through, which are disclosed herein. In some embodiments, the method of treating cancer in a subject includes administering amlexanox in combination with compounds that inhibit NMD complex, which are disclosed herein. In some embodiments, the method includes administering amlexanox in combination with compounds that promote PTC read-through and compounds that inhibit NMD complex. In some embodiments, the methods disclosed herein involve generating an immune response in an individual by inducing the expression of neoantigens on the surface of abnormal (such as proliferative) cells or cancer cells.

In some embodiments, the method of treating cancer in a subject includes administering amlexanox in combination with molecules that inhibit at least one immune checkpoint protein disclosed herein. In some embodiments, the method includes administering a therapeutically effective amount of amlexanox and a therapeutically effective amount of at least one checkpoint inhibitor.

Immune checkpoints are proteins in the immune system that either turn up a signal (co-stimulatory molecules) or turn down a signal. Checkpoint modulators are designed to overcome one of the primary ways a cancer cell evades detection by the immune system. T lymphocytes routinely monitor cells for signs of disease. If an antigen on the surface of a cell suggests the cell is abnormal, the T cell will initiate an immune response that includes increasing the expression of additional molecules to prevent the immune response from damaging normal tissues in the body. These proteins are known as immune checkpoints.

Cancer cells often use immune checkpoint proteins to evade or suppress attack by the immune system. Thus, expression of immune checkpoint proteins on the surface of cancers cells prevents immune cells such as T cells from recognizing them as "foreign" or "abnormal." Consequently, checkpoint inhibitors are compounds which block inhibitory immune checkpoint proteins leading to the activation of the immune system via T cell recognition.

Any molecule capable of inhibiting one or more immune checkpoint proteins can be used in the methods disclosed herein. Such molecules are called checkpoint inhibitors. These include, without limitation, antibodies or functional fragments thereof, inhibitory polypeptides, small molecule chemical compounds, and/or inhibitory nucleic acids (such as, but not limited to, antisense oligonucleotides, small inhibitory RNAs (siRNAs), small hairpin RNAs (shRNAs), and/or catalytic nucleic acids such as ribozymes). Immune checkpoint proteins suitable for targeting by checkpoint inhibitors for use in any of the methods disclosed herein include, without limitation, one or more of the adenosine A2A receptor (A2AR), B7-H3 (a.k.a. CD276; e.g., MGA271), cytotoxic T-lymphocyte-associated protein 4 (CTLA4; a.k.a. CD152; e.g., ipilimumab; AGEN-1884 (Agenus)), programmed cell death ligand 1 (PD-L1; a.k.a. CD274; e.g., MDX-1105 (Bristol Myers Squibb), WBP-3155 (C-stone), LY3300054 (Eli Lilly)), programmed cell death protein 1 (PD-1; a.k.a. CD279; e.g., pembrolizumab, SHR-1210 (Incyte), STI-A1110 (Sorrento), REGN2810 (Regeneron), CT-011 (pidilizumab; Curetech), PDR-001 (Novartis), BGB-A317 (BeiGene), TSR-042 (Tesaro), ENUMC-8 (Enumeral), MGD-013 (Macrogenics; bispecific antibody for PD1 and Lag3), B7-H4 (a.k.a. VTCN1), T-cell immunoglobulin and mucin-domain containing-3 (TIM3; a.k.a. HAVCR2), B and T Lymphocyte Attenuator (BTLA; a.k.a. CD272), indoleamine-pyrrole 2,3-dioxygenase (IDO), killer-cell immunoglobulin-like receptors (KIRs; e.g., liri-lumab), lymphocyte-activation gene 3 (LAG-3; e.g., BMS-986016), T cell immunoreceptor with Ig and ITIM domains (TIGIT; a.k.a. WUCAM and Vstm3), ILT-3, ILT-4, and/or V-domain Ig suppressor of T cell activation (VISTA).

In some embodiments, the checkpoint inhibitor is an antagonistic antibody, such as, but not limited to, one or more of ipilimumab (Bristol-Myers Squibb), nivolumab (Bristol-Myers Squibb), Pembrolizumab (Merck) durvalumab (Medimmune), atezolizumab (Genentech/Roche), tremelimumab (Medimmune), and/or avelumab (Pfizer).

In some embodiments, immune co-stimulatory molecules can be used in combination with amlexanox and checkpoint inhibitors. Immune co-stimulatory molecules are immune modulators and belong to members of the tumor necrosis factor (TNF) receptor superfamily and the B7-CD28 superfamily. Non-limiting examples include, without limitation, activators of CD27, GITR, B7-H3, CD28, CD40, interleukin-2 receptor subunit beta (ILR2P; a.k.a. CD122; e.g., NKTR-214), CD137 (a.k.a. TNFRSF9, 4-1BB, and induced by lymphocyte activation (ILA)), ICOS, and/or OX40 (a.k.a. CD134 and TNFRSF4). Many of these activators are agonistic antibodies, such as CDX-1 127, TGN1412, MED10562, MEDI6469, and MEDI6383.

In some embodiments, the method of treating cancer in a subject includes administering amlexanox in combination with one checkpoint inhibitor disclosed herein. In some embodiments, the method includes administering amlexanox in combination with two checkpoint inhibitors disclosed herein. In some embodiments, the method includes administering amlexanox in combination with one checkpoint inhibitor and one immune co-stimulatory molecule disclosed herein. In some embodiments, the method includes administering amlexanox in combination with one of the checkpoint inhibitors described in Table 1 and one of the immune co-stimulatory molecules described in Table 1:

TABLE 1

| Checkpoint inhibitor | Immune co-stimulatory molecule |
| --- | --- |
| anti-PD-1 antibody | anti-CD27 antibody (eg., CDX-1127) |
| anti-PD-L1 antibody | anti-CD28 antibody |
| anti-CTLA4 antibody | anti-CD-40 antibody |
| anti-A2AR antibody | anti-OX40 antibody (eg., MEDI6469, MEDI0562, MEDI6383) |
| anti-KIR antibody | |
| anti-LAG3 antibody | CD122 specific cytokine (eg., NKTR-214) |
| anti-B7-H3 antibody | Anti-GITR antibody |
| | ICOS agonist |
| | CD137 agonist |

In some embodiments, the method of treating cancer in a subject includes administering amlexanox in combination with one immune co-stimulatory molecule disclosed herein. In some embodiments, the method includes administering amlexanox in combination with two immune co-stimulatory molecules disclosed herein.

The method also provides methods for reducing the risk of post-surgical complications comprising administering an effective amount of amlexanox in combination with molecules that inhibit at least one checkpoint protein before, during, or after surgery, and in specific non-limiting embodiments, surgery to treat cancer.

The disclosure also provides methods for preventing occurrence, preventing or delaying recurrence, or reducing the rate of recurrence of a cancer comprising directly administering to a patient in need thereof an effective amount of amlexanox described herein in combination with molecules that inhibit at least one checkpoint protein. In some embodiments, combination of amlexanox and checkpoint inhibitors can be used as adjuvant therapy.

The disclosure also provides methods for sensitizing a tumor or cancer to one or more other anticancer agents comprising administering amlexanox in combination with molecules that inhibit at least one checkpoint protein. The anticancer agents may be administered prior to, overlapping with, concurrently, and/or after administration of amlexanox and checkpoint inhibitors. In some embodiments, amlexanox and checkpoint inhibitors are administered to the subject before the cancer treatment, concurrently with the cancer treatment, post-treatment, or during remission of the cancer. When administered concurrently, the amlexanox/checkpoint inhibitors and other anticancer agent may be administered in a single formulation or in separate formulations, and if separately, then optionally, by different modes of administration. Accordingly, the combination of amlexanox/checkpoint inhibitors and one or more other anticancer agents may synergistically act to combat the tumor or cancer.

Indeed, administration of an effective amount of amlexanox and/or checkpoint inhibitors to a patient in need of such treatment may result in reduced doses of another anticancer agent having clinically significant efficacy. Such efficacy of the reduced dose of the other anticancer agent may not be observed absent administration with amlexanox and/or check point inhibitors. Accordingly, the present invention provides methods for treating a tumor or cancer comprising administering a reduced dose of one or more other anticancer agents.

In some embodiments, the anticancer agents may be tamoxifen, toremifen, raloxifene, droloxifene, iodoxyfene, megestrol acetate, anasfrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, Irinotecan, topotecan, an epothilone, gefitinib, erlotinib, sorafenib, angiogenesis inhibitors, EGF inhibitors, VEGF inhibitors, CDK inhibitors, cytokines, Her1 and Her2 inhibitors, and monoclonal antibodies.

In another embodiment, amlexanox and checkpoint inhibitors are administered in combination with a regimen of radiation therapy. The therapy may also comprise surgery and/or chemotherapy. For example, the amlexanox and checkpoint inhibitors may be administered in combination with radiation therapy and cisplatin (Platinol), fluo-rouracil (5-FU, Adrucil), carboplatin (Paraplatin), and/or paclitaxel (Taxol). Treatment with amlexanox/checkpoint inhibitors may allow use of lower doses of radiation and/or less frequent radiation treatments, which may for example, reduce the incidence of severe sore throat that impedes swallowing function potentially resulting in undesired weight loss or dehydration.

In some embodiments disclosed herein are methods for inhibiting tumor growth in an individual by administering amlexanox and one or more molecules (such as an antibody, e.g. a monoclonal antibody) that inhibits an immune checkpoint protein. The combination of amlexanox added to an immune checkpoint inhibitor are as effective or are more effective in inhibiting tumor growth as compared to a combination of two or more antibody-based immune checkpoint inhibitory therapies administered without a combination of amlexanox. Additionally, administration of a combination of amlexanox and molecule that inhibits an immune checkpoint protein according to the methods described herein results in decreased side effects and adverse events (for example any of about 10%, 20%, 30%, 40%, 50%, 60%, 70%, 80%, 90%, or 100% decreased side effects and adverse events, including all values falling in between these percentages) compared to administration of two or more antibody-based immune checkpoint inhibitory therapies (for example, the combination of anti-PD-1 and anti-CTLA-4 antibodies) alone.

In some embodiments, the methods involve administering amlexanox in combination with molecules that inhibit one or more of the following: PD-1, PD-L1, and CTLA-4. In some embodiments, the amlexanox of Formula I is administered in combination with molecules that inhibit one or more of the following: PD-1, PD-L1, and CTLA-4. In some embodiments, the amlexanox of Formula II is administered in combination with molecules that inhibit one or more of the following: PD-1 and CTLA-4. In some embodiments, the amlexanox of Formula III is administered in combination with molecules that inhibit one or more of the following: PD-1, PD-L1, and CTLA-4. In some embodiments, the molecules that inhibit PD-1, PD-L1, and CTLA-4 are antibodies.

In some embodiments, the method includes administering amlexanox in combination with anti-PD-1 antibodies. In some embodiments, the method includes administering amlexanox in combination with anti-PD-L1 antibodies. In some embodiments, the method includes administering amlexanox in combination with anti-CTLA-4 antibodies. In some embodiments, the method includes administering amlexanox in combination with anti-PD-1 and anti-CTLA-4 antibodies. In some embodiments, the method includes administering amlexanox in combination with anti-PD-L1 and anti-CTLA-4 antibodies.

In some embodiments, amlexanox is administered to the individual in any of the following ranges: about 0.5 to about 1 mg/kg, about 0.5 to about 2 mg/kg, about 0.5 to about 3 mg/kg, about 0.5 to about 4 mg/kg, about 0.5 to about 5 mg/kg, about 0.5 to about 10 mg/kg, about 0.5 to about 20 mg/kg, about 0.5 to about 50 mg/kg, about 1 to about 10 mg/kg, about 1 to about 50 mg/kg, about 10 to about 100 mg/kg, about 10 to about 150 mg/kg, about 50 to about 175 mg/kg, about 175 to about 200 mg/kg, about 200 to about 225 mg/kg, about 225 to about 250 mg/kg, about 250 to about 300 mg/kg, about 300 to about 350 mg/kg, about 350 to about 400 mg/kg, about 400 to about 450 mg/kg, or about 450 to about 500 mg/kg. The dose administered may be every day, every 2 days, every 3 days, every 4 days, every 5 days, every week, every 2 weeks, every 3 weeks, every 4 weeks, and so on until there is remission.

In some embodiments, the checkpoint inhibitors are administered at dosages: 0.1 mg/kg, 0.2 mg/kg, 0.3 mg/kg, 0.4 mg/kg, 0.5 mg/kg, 1.3 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 33.3 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg.

In a preferred embodiment, antibodies against PD-1, PD-L1 and CTLA-4 are administered at a dose of 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg. The dose administered may be every day, every 2 days, every 3 days, every 4 days, every 5 days, every week, every 2 weeks, every 3 weeks, every 4 weeks, and so on until there is remission.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 3 days.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every week.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 10 days.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 2 weeks.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 3 weeks.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 4 weeks.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 8 weeks.

In one embodiment, amlexanox is administered at a dose from about 1 mg/kg to 50 mg/kg daily, and anti-PD-1 antibodies and anti-CTLA-4 antibodies are each administered at a dose from about 1 mg/kg to about 15 mg/kg every 12 weeks.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 3 days.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every week.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 10 days.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 2 weeks.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 3 weeks.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 4 weeks.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 8 weeks.

In one embodiment, amlexanox is administered at a dose from about 1 mg/kg to 50 mg/kg daily, and anti-PD-L1 antibodies and anti-CTLA-4 antibodies are each administered at a dose from about 1 mg/kg to about 15 mg/kg every 12 weeks.

In one embodiment, amlexanox is administered at a dose from about 1 mg/kg to 50 mg/kg daily, and anti-PD-1 antibodies are administered at a dose from about 100 mg to about 1500 mg every 3 days. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every 3 days.

In one embodiment, amlexanox is administered at a dose from about 1 mg/kg to 50 mg/kg daily, and anti-PD-1 antibodies are administered at a dose from about 100 mg to about 1500 mg every week. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every week.

In one embodiment, amlexanox is administered at a dose from about 1 mg/kg to 50 mg/kg daily, and anti-PD-1 antibodies are administered at a dose from about 100 mg to about 1500 mg every 2 weeks. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every 2 weeks.

In one embodiment, amlexanox is administered at a dose from about 1 mg/kg to 50 mg/kg daily, and anti-PD-1 antibodies are administered at a dose from about 100 mg to about 1500 mg every 4 weeks. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every 4 weeks.

In one embodiment, amlexanox is administered at a dose from about 1 mg/kg to 50 mg/kg daily, and anti-PD-1 antibodies are administered at a dose from about 100 mg to about 1500 mg every 8 weeks. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every 8 weeks.

In one embodiment, amlexanox is administered at a dose from about 1 mg/kg to 50 mg/kg daily, and anti-PD-1 antibodies are administered at a dose from about 100 mg to about 1500 mg every 12 weeks. In one embodiment, amlexanox is administered at a dose from about 1 mg/kg to 50 mg/kg daily, and anti-PD-1 antibodies and anti-CTLA-4 antibodies are each administered at a dose from about 100 mg to about 1500 mg every 12 weeks.

In one embodiment, amlexanox is administered at a dose from about 1 mg/kg to 50 mg/kg daily, and anti-PD-L1 antibodies are administered at a dose from about 100 mg to about 1500 mg every 3 days. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every 3 days.

In one embodiment, amlexanox is administered at a dose from about 1 mg/kg to 50 mg/kg daily, and anti-PD-L1 antibodies are administered at a dose from about 100 mg to about 1500 every week. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every week.

In one embodiment, amlexanox is administered at a dose from about 1 mg/kg to 50 mg/kg daily, and anti-PD-L1 antibodies are administered at a dose from about 100 mg to about 1500 an every 2 weeks. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every 2 weeks.

In one embodiment, amlexanox is administered at a dose from about 1 mg/kg to 50 mg/kg daily, and anti-PD-L1 antibodies are administered at a dose from about 100 mg to about 1500 every 4 weeks. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every 4 weeks.

In one embodiment, amlexanox is administered at a dose from about 1 mg/kg to 50 mg/kg daily, and anti-PD-L1 antibodies are administered at a dose from about 100 mg to about 1500 every 8 weeks. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every 8 weeks.

In one embodiment, amlexanox is administered at a dose from about 1 mg/kg to 50 mg/kg daily, and anti-PD-L1 antibodies are administered at a dose from about 100 mg to about 1500 every 12 weeks. In one embodiment, amlexanox is administered at a dose from about 1 mg/kg to 50 mg/kg daily, and anti-PD-L1 antibodies and anti-CTLA-4 antibodies are each administered at a dose from about 100 mg to about 1500 mg every 12 weeks.

In one embodiment, amlexanox is administered at a dose from about 1 mg/kg to 50 mg/kg daily, and anti-CTLA-4 antibodies are administered at a dose from about 100 mg to about 1500 every 3 days. In one embodiment, amlexanox is administered at a dose from about 1 mg/kg to 50 mg/kg daily, and anti-PD-1 antibodies are administered at a dose from about 100 mg to about 1500 every 3 days. In one embodiment, amlexanox is administered at a dose from about 1 mg/kg to 50 mg/kg daily, and anti-PD-L1 antibodies are administered at a dose from about 100 mg to about 1500 every 3 days.

In one embodiment, amlexanox is administered at a dose from about 1 mg/kg to 50 mg/kg daily, and anti-CTLA-4 antibodies are administered at a dose from about 100 mg to about 1500 every week. In one embodiment, amlexanox is administered at a dose from about 1 mg/kg to 50 mg/kg daily, and anti-PD-1 antibodies are administered at a dose from about 100 mg to about 1500 every week. In one embodiment, amlexanox is administered at a dose from about 1 mg/kg to 50 mg/kg daily, and anti-PD-L1 antibodies are administered at a dose from about 100 mg to about 1500 every week.

In one embodiment, amlexanox is administered at a dose from about 1 mg/kg to 50 mg/kg daily, and anti-CTLA-4 antibodies are administered at a dose from about 100 mg to about 1500 every 2 weeks. In one embodiment, amlexanox is administered at a dose from about 1 mg/kg to 50 mg/kg daily, and anti-PD-1 antibodies are administered at a dose from about 100 mg to about 1500 every 2 weeks. In one embodiment, amlexanox is administered at a dose from about 1 mg/kg to 50 mg/kg daily, and anti-PD-L1 antibodies are administered at a dose from about 100 mg to about 1500 every 2 weeks.

In one embodiment, amlexanox is administered at a dose from about 1 mg/kg to 50 mg/kg daily, and anti-CTLA-4 antibodies are administered at a dose from about 100 mg to about 1500 every 4 weeks. In one embodiment, amlexanox is administered at a dose from about 1 mg/kg to 50 mg/kg daily, and anti-PD-1 antibodies are administered at a dose from about 100 mg to about 1500 every 4 weeks. In one embodiment, amlexanox is administered at a dose from about 1 mg/kg to 50 mg/kg daily, and anti-PD-L1 antibodies are administered at a dose from about 100 mg to about 1500 every 4 weeks.

In one embodiment, amlexanox is administered at a dose from about 1 mg/kg to 50 mg/kg daily, and anti-CTLA-4 antibodies are administered at a dose from about 100 mg to about 1500 every 8 weeks. In one embodiment, amlexanox is administered at a dose from about 1 mg/kg to 50 mg/kg daily, and anti-PD-1 antibodies are administered at a dose from about 100 mg to about 1500 every 8 weeks. In one embodiment, amlexanox is administered at a dose from about 1 mg/kg to 50 mg/kg daily, and anti-PD-L1 antibodies are administered at a dose from about 100 mg to about 1500 every 8 weeks.

In one embodiment, amlexanox is administered at a dose from about 1 mg/kg to 50 mg/kg daily, and anti-CTLA-4 antibodies are administered at a dose from about 100 mg to about 1500 every 12 weeks. In one embodiment, amlexanox is administered at a dose from about 1 mg/kg to 50 mg/kg daily, and anti-PD-1 antibodies are administered at a dose from about 100 mg to about 1500 every 12 weeks. In one embodiment, amlexanox is administered at a dose from about 1 mg/kg to 50 mg/kg daily, and anti-PD-L1 antibodies are administered at a dose from about 100 mg to about 1500 every 12 weeks.

In another embodiment, amlexanox in combination with molecules that inhibit one or more immune checkpoint proteins administered according to any of the methods disclosed herein provide at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% tumor inhibitory effect when compared to tumors that are not treated with amlexanox and checkpoint inhibitors.

The compounds and molecules disclosed herein can be administered in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the molecules of the present disclosure (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams. In some embodiments, amlexanox and checkpoint inhibitors can be administered directly to the tumor site.

In some embodiments, amlexanox and checkpoint inhibitors can be administered directly to the tumor site. In some embodiments, amlexanox is administered at the tumor site and checkpoint inhibitors are administered intravenously. In some embodiments, amlexanox is administered at the tumor site, followed by oral administration of amlexanox and intravenous administration of checkpoint inhibitors.

In some embodiments, the method includes administering amlexanox orally in combination with intratumoral injection of immune modulators, without limitation, selected from oncolytic adenovirus, CDNs, TLR agonists, TNFR superfamily agonists, and epigenetic modulatory compounds. In some embodiments, the method includes administering amlexanox orally in combination with intratumoral injection of immune modulators (oncolytic adenovirus, CDNs, TLR agonists, TNFR superfamily agonists, and epigenetic modulatory compounds), and further administration of checkpoint inhibitors intravenously. In some embodiments, the method includes administering amlexanox orally in combination with intratumoral injection of immune modulators (oncolytic adenovirus, CDNs, TLR agonists, TNFR superfamily agonists, and epigenetic modulatory compounds), and further administration of immune co-stimulatory molecules intravenously. In some embodiments, the method includes administering amlexanox orally in combination with chemotherapy and intratumoral injection of immune modulators. In some embodiments, the method includes administering amlexanox orally in combination with radiotherapy and intratumoral injection of immune modulators.

In some embodiments, amlexanox and checkpoint inhibitors are administered intravenously. In some embodiments, amlexanox is administered orally and checkpoint inhibitors are administered intravenously. In some embodiments, amlexanox and checkpoint inhibitors are administered orally. In some embodiments, amlexanox and checkpoint inhibitors are administered simultaneously or sequentially. For example, amlexanox can be administered first followed by administering antibodies to PD-1, PD-L1, and CTLA-4. In some embodiments, antibodies to PD-1, PD-L1, and CTLA-4 can be administered first, followed by administration of amlexanox.

Specific modes of administration will depend on the indication. The selection of the specific route of administration and the dose regimen is to be adjusted or titrated by the clinician according to methods known to the clinician in order to obtain the optimal clinical response. The amount of compounds to be administered is that amount which is therapeutically effective. The dosage to be administered will depend on the characteristics of the subject being treated, e.g., the particular animal or human being treated, age, weight, health, types of concurrent treatment, if any, and frequency of treatments, and can be easily determined by one of skill in the art (e.g., by the clinician).

In another embodiment, a method of killing cancer cells may comprise contacting the cancer cells with a composition comprising amlexanox in combination with a molecule that inhibits at least one immune checkpoint protein. In some embodiments, the method may be in vitro or in vivo. In some embodiments, the molecule that inhibit checkpoint proteins may be antibodies against PD-1, PD-L1, and CTLA-4. In some embodiments, the cancer cell is selected from colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia, chronic leukemia; polycythemia vera, lymphoma, multiple myeloma, Waldenstrom's macroglobulinemia, and heavy chain disease.

In an additional embodiment, a method of killing cancer stem cells may comprise contacting the cancer stem cells with a composition comprising amlexanox in combination with a molecule that inhibits at least one immune checkpoint protein. In some embodiments, the method may be in vitro or in vivo. In some embodiments, the molecule that inhibit checkpoint proteins may be antibodies against PD-1, PD-L1, and CTLA-4. In some embodiments, the method includes contacting cancer stem cells with amlexanox and molecular adjuvants, such as TNF receptor superfamily (TNFRSF) agonists, GM-CSF, Toll-like receptor (TLR) ligands, and intracellular DNA sensor agonists, such as cyclic dinucleotides (CDNs) and CpG motifs.

In a further embodiment, a method for inducing the expression of one or more neoantigens on the surface of an abnormal cell includes contacting the abnormal cell with amlexanox in combination with a molecule that inhibits at least one immune checkpoint protein. In some embodiments, the method may be in vitro or in vivo. In some embodiments, the amlexanox of Formula I is contacted in combination with molecules that inhibit one or more of the following: PD-1, PD-L1, and CTLA-4. In some embodiments, the amlexanox of Formula II is contacted in combination with molecules that inhibit one or more of the following: PD-1 and CTLA-4. In some embodiments, the amlexanox of Formula III is contacted in combination with molecules that inhibit one or more of the following: PD-1, PD-L1, and CTLA-4. In some embodiments, the molecules that inhibit PD-1, PD-L1, and CTLA-4 are antibodies.

In another embodiment, a method for generating an immune response in an individual in need thereof comprising administering to the individual a therapeutically effective amount of a compound that both promotes premature termination codon (PTC) read-through in an mRNA and inhibits the nonsense-mediated decay (NMD) of an mRNA. In some embodiments, the compound is amlexanox. In some embodiments, the method further includes administering molecules that inhibit immune checkpoint proteins. In some embodiments, the checkpoint proteins are PD-1 and CTLA-4. In some embodiments, the methods involve administering amlexanox in combination with molecules that inhibit one or more of the following: PD-1, PD-L1, and CTLA-4. In some embodiments, the amlexanox of Formula I is administered in combination with molecules that inhibit one or more of the following: PD-1, PD-L1, and CTLA-4. In some embodiments, the amlexanox of Formula II is administered in combination with molecules that inhibit one or more of the following: PD-1 and CTLA-4. In some embodiments, the amlexanox of Formula III is administered in combination with molecules that inhibit one or more of the following: PD-1, PD-L1, and CTLA-4. In some embodiments, the molecules that inhibit PD-1, PD-L1, and CTLA-4 are antibodies.

In some embodiments, a method for generating an immune response in an individual in need thereof comprising administering to the individual a therapeutically effective amount of a compound that promotes PTC read-through. In some embodiments, a method of treating cancer in a subject includes administering to the individual a therapeutically effective amount of a compound that promotes PTC read-through.

Any compound capable of promoting read-through of an mRNA bearing a PTC is suitable for use in the present method. To date, most reported PTC read-through compounds that are active in mammalian cells have belonged to the aminoglycoside class of antibiotics. Certain types of aminoglycosides can induce ribosomes to read-through PTC mutations via insertion of a random amino acid by a near-cognate transfer RNA (tRNA). The therapeutic potential of aminoglycosides has been evaluated in the laboratory for different genetic models, such as cystic fibrosis. In some embodiments, the PTC read-through compound is ataluren (formerly known as PTC 124).

In some embodiments, the compound that promotes PTC read-through is a 1,2,4-oxadiazole benzoic acid compound of formula IV:

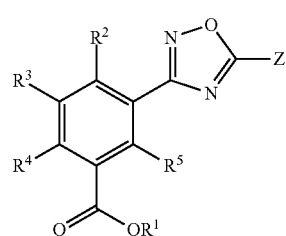

(IV)

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstitued alkenyl, substituted or unsubstituted heterocycle, substituted or unsubstituted arylalkyl;

R1 is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —(CH2CH2)nOR6 or any biohydrolyzable group;

R2, R3, R4, R5 and R6 are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, CF3, OCF3, OCHF2, CN, COOH, COOR7, SO2R7, NO2, NH2, or N(R7)2;

each occurrence of R7 is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or CF3; and n is an integer from 1 to 7.

In a further embodiment, the compound that promotes PTC read-through is 3-[5-(2-Fluorophenyl)-1,2,4-oxadiazol-3-yl]benzoic acid.

In certain embodiments, the compounds for promoting PTC read-through for use in the methods disclosed herein are:

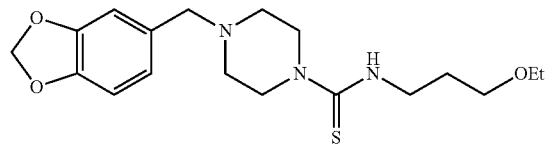

GJ071

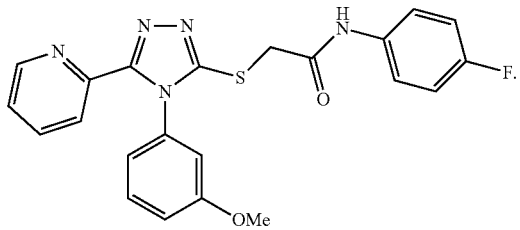

GJ072

In some embodiments, the compound for promoting PTC read-through suitable for use in any of the methods disclosed herein is an aminoglycoside such as, without limitation, amikacin, G418 (geneticin), gentamicin, or paromomycin. In other embodiments, the PTC read-through compound is an aminoglycoside derivative such as, without limitation, NB54, NB74, NB84, or TC007. In further embodiments, the compound for promoting PTC read-through is a non-aminoglycoside such as, without limitation, negamycin or tylosin.

In further embodiments, the compounds for promoting PTC read-through for use in the methods disclosed herein are:

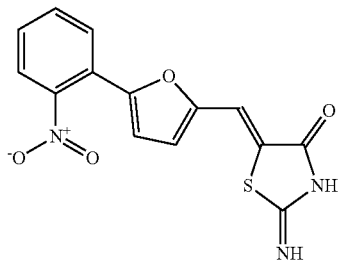

RTC#13

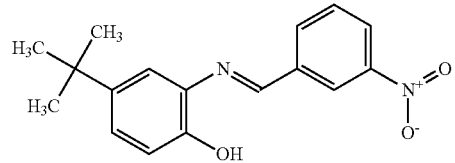

RTC#14

Further PTC read-through drugs appropriate for use in the methods disclosed herein include, without limitation, isepamicin, tobramycin, RTC #1, RTC #2, RTC #3, RTC #4, RTC #7, RTC #9, RTC #10, RTC #11, RTC #16, RTC #17, clitocin, macrolide spiramycin, macrolide josamycin, macrolide tylosin, NB30, streptomycin, hygromycin, puromycon, lividomycin, TC001, TC003, TC032, JL022, JL023, hygromycin B, kanamycin A, kanamycin B and its "JL" derivatives, neomycin and its "TC" derivatives, paroamine and its synthetic derivatives, paromomycin and its "NB" derivatives, or oleandomycon, Negamycin, sisomicin, garamine, 2-deoxystreptamine, gentamycin, gentamycin B1, gentamycin C1, gentamycin C1a, gentamycin C2, gentamycin C2a, and gentamycin C2b.

In yet other embodiments, the compounds for promoting PTC read-through for use in the methods disclosed herein can be negamycin derivatives, such as, without limitation:
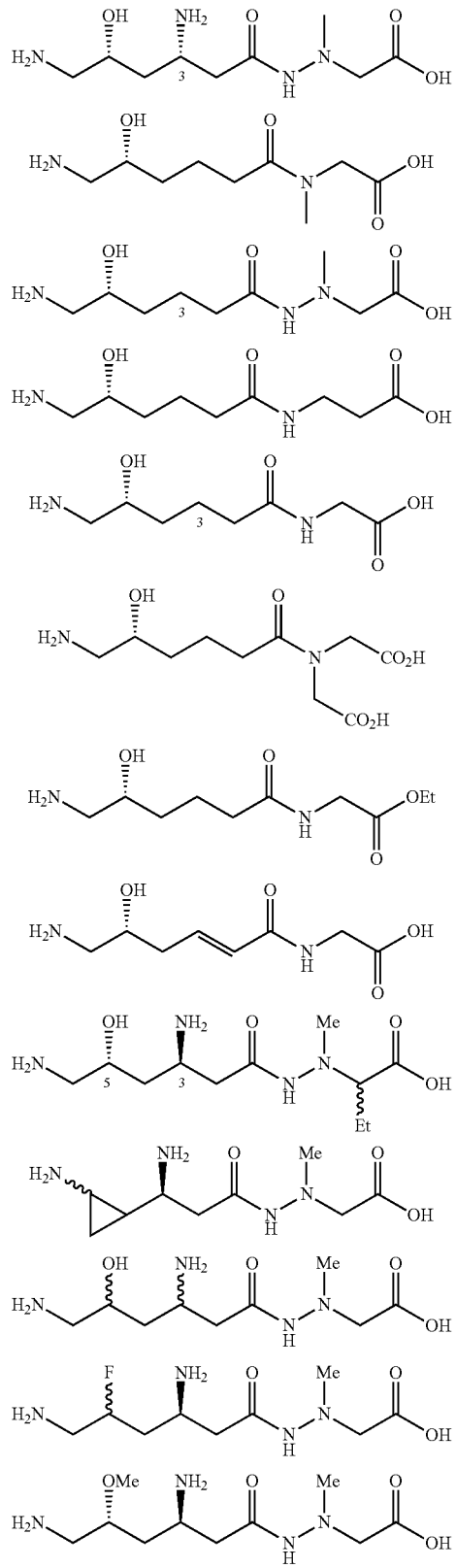
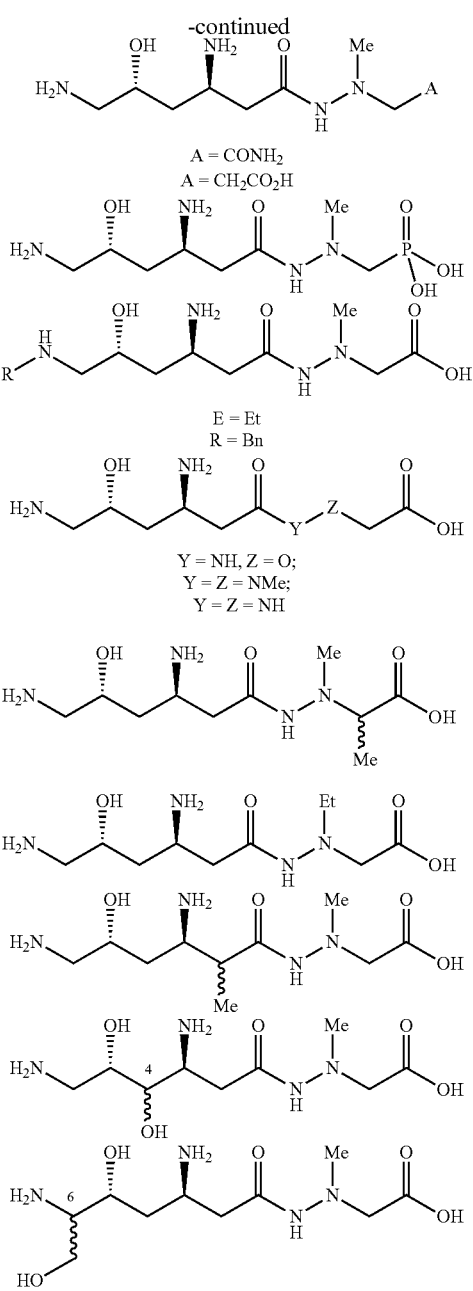
In some embodiments, compounds that promote PTC read-through are represented by Formula V:
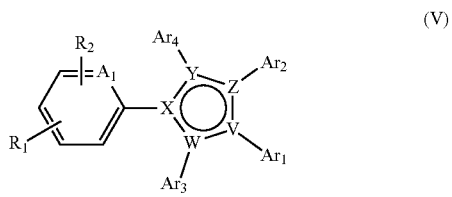
wherein:
A1 is C, CH or N;
V and X are independently selected from N or C;
W is selected from N, C or CH;

wherein at least one of V, W, or X is N, and wherein if W is N, at least one of V or X also N;

Y and Z are independently selected from N, C, C-Rc, C═O, C═S, wherein Rc is H, CH3, or NH2; with the proviso that when one of Y or Z is C═O or C═S, the other may also be selected from NH, S, or O;

R1 is carboxy, cyano, or a carbonyl group which is optionally substituted with a $C_1$-$C_4$ alkoxy group, R2 is absent or a nitro;

Ar1 is a C1 to C4 alkyl which is optionally substituted with a R group; a C6 to C10 aryl which is optionally substituted with one, two or three independently selected R groups; a five to ten membered heterocycle which is optionally substituted with one, two or three independently selected R groups; together with Ar2 and the heterocycle to which Ar1 and Ar2 are attached form a ring structure selected from Ar1-2; or together with Ar3 and the heterocycle to which Ar1 and Ar3 are attached form a ring structure selected from Ar1-3;

Ar2 is absent or together with Ar1 and the heterocycle to which Ar1 and Ar2 are attached form a ring structure selected from Ar1-2;

Ar3 is absent or together with Ar1 and the heterocycle to which Ar1 and Ar3 are attached form a ring structure selected from Ar1-3;

Ar4 is absent or is a C1-C4 alkyl, a C1-C4 alkoxy, or a C1-C4 thioalkyl, any of which together with A1 forms a four to seven membered carbocycle or heterocycle;

R is hydrogen; a —Ra group; or two R groups, where R may also include an oxy group, together with the phenyl or heterocycle to which they are attached form a ring structure selected from RR;

wherein:

Ar1-2 and Ar1-3 are selected from an eleven to fourteen membered hetero-tricycle ring structure optionally substituted with one or more halogens, C1-C4 alkyl groups, C1-C4 haloalkyl groups, C1-C4 alkoxy groups optionally substituted with a halogen or a C1-C4 alkoxy group, C1-C4 haloalkoxy groups, or amino groups optionally substituted with a carbonyl group which is substituted with a C1-C4 alkyl group;

RR is a nine to ten membered bicyclic ring structure optionally substituted with one or more halogens, C1-C4 alkyl groups, C1-C4 haloalkyl groups, C1-C4 alkoxy groups, oxo groups, or C1-C4 haloalkoxy groups;

Ra is selected from the group consisting of: a hydroxy group; a halogen; a C1-C4 alkyl which is optionally substituted with one or more independently selected halogen or hydroxy groups; a C1-C4 alkoxy which is optionally substituted with one or more independently selected halogen or phenyl groups; a C4-C8 cycloalkyl which is optionally substituted with one or more independently selected C1-C4 alkyl groups; an —Rb group; a O—Rb group; a four to six-membered heterocycle which is optionally substituted with one or more independently selected C1-C4 alkyl, oxo, or —Rb groups; a nine to ten membered heterocycle having two ring structures; a carbonyl which is optionally substituted with a hydroxy, a C1-C4 alkyl, or a C1-C4 alkoxy group; a carbamoyl which is optionally substituted with one or two C1-C4 alkyl groups; a nitro group; a cyano group; a thio which is optionally substituted with a hydroxy, a C1-C4 alkyl, or —Rb group; a sulfonyl which is optionally substituted with a hydroxy, a C1-C4 alkyl, or —Rb group; or an amino which is optionally substituted with one or two independently selected C1-C4 alkyl, sulfonyl, or carbonyl groups, wherein the aminosulfonyl group is optionally substituted with a hydroxy, a C1-C4 alkyl, or —Rb group and wherein the aminocarbonyl group is optionally substituted with a C1-C4 alkyl, a C1-C4 haloalkyl, a benzoxy, or an amino group which is optionally substituted with an —Rb group;

wherein —Rb is a C6-C8 aryl which is optionally substituted with one or more of the following: a hydroxy, a halogen, a C1-C4 alkyl group, a C1-C4 haloalkyl group, a C1-C4 alkoxy group, or an amino group which is optionally substituted with one or more C1-C4 alkyl groups;

or a pharmaceutically acceptable salt, hydrate, solvate, clathrate, racemate, stereoisomer, or polymorph of said compound of In some embodiments, compounds that promote PTC read-through are represented by:

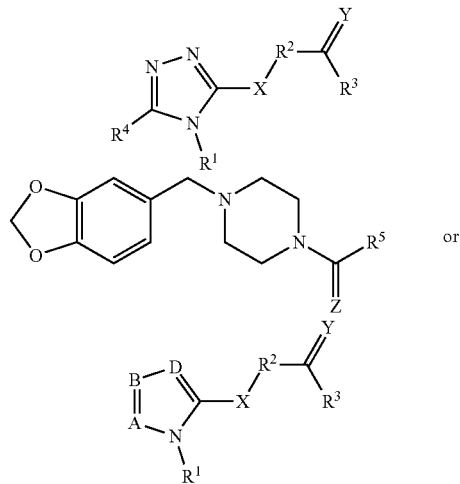

wherein:

A is either nitrogen or carbon, with the carbon being substituted with any aryl or heteroaryl group, any alkyl or substituted alkyl, any arylalkyl or heteroarylalkyl, any functionalized alkyl or aryl (or heteroaryl) group;

B is either nitrogen or carbon, with the carbon being either unsubstituted or substituted with halo, pseudohalo, alkyl, alkoxy, or thioalkoxy groups;

D is either nitrogen or carbon, with the carbon being either unsubstituted or substituted with halo, pseudohalo, alkyl, alkoxy, or thioalkoxy groups;

R1 is any aryl or heteroaryl group, any alkyl or substituted alkyl, any arylalkyl or heteroarylalkyl, any functionalized alkyl or aryl (or heteroaryl) group;

R2 is a methylene unit (CH2)n where n is 1, 2, or 3; or the carbon atom or atoms of a ring, either carbocyclic or heterocyclic, of from 3-10 atoms;

R3 is any aryl or heteroaryl group, any alkyl or substituted alkyl, any arylalkyl or heteroarylalkyl, any functionalized alkyl or aryl (or heteroaryl) group, hydroxy, alkoxy, or —NR6R6a;

R4 is any aryl or heteroaryl group, any alkyl or substituted alkyl, any arylalkyl or heteroarylalkyl, any functionalized alkyl or aryl (or heteroaryl) group;

R5 is any aryl or heteroaryl group, any alkyl or substituted alkyl, any arylalkyl or heteroarylalkyl, any functionalized alkyl or aryl (or heteroaryl) group, or —NR5aR5b;

R5a is hydrogen or alkyl;

R5b is alkyl, alkoxyalkyl, alkenyl, aryl, arylalkyl, heteroaryl, or heteroarylalkyl, where the aryl and heteroaryl, either alone or as part of arylalkyl and heteroarylalkyl, are optionally substituted with 1, 2, or 3 groups independently selected from alkyl, halo, haloalkyl, hydroxy, and alkoxy;

R6 is hydrogen or alkyl;

R6a is —NHC(O)(arylalkyl), alkyl, hydroxyalkyl, cycloalkyl, heteroaryl, or aryl where the aryl, arylalkyl, and heteroaryl are optionally substituted with 1, 2, or 3 groups selected from hydroxy, halo, haloalkyl, alkyl, alkoxy, carboxy, or alkoxycarbonyl;

X is oxygen, sulfur, NH or N-substituted; and

Y is taken from the group, oxygen, sulfur, NH or N-substituted, or carbon, substituted or unsubstituted; and Z is oxygen, sulfur, NH or N-substituted; or a pharmaceutically acceptable salt thereof.

In some embodiments, a compound that promotes PTC read-through is represented by Formula VI:

$$(VI)$$

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstituted alkenyl, substituted or unsubstituted heterocycle, substituted or unsubstituted arylalkyl, or aryloxyalkyl; and X1, X2, X3 and X4 are independently H or OH, and at least one of X1, X2, X3 or X4 is OH.

In a particular embodiment, Z is substituted aryl. In another embodiment, Z is halo substituted aryl. In another embodiment, Z is fluoro substituted aryl. In another embodiment, Z is substituted phenyl. In another embodiment, Z is halo substituted phenyl. In another embodiment, Z is fluoro substituted phenyl.

In some embodiments, a compound that promotes PTC read-through is represented by Formula VII:

$$(VII)$$

or a pharmaceutically acceptable salt, hydrate, solvate, clathrate, racemate or stereoisomer thereof, wherein:

Z is substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl;

X is CH2, O, S or NH;

R1 is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl;

R2 is substituted or unsubstituted alkyl, carboxy, amido, acyl, alkylcarbonyl, halogen, a biohydrolyzable group, OP(O)3 2-, O[P(O)3]2 3-, O[P(O)3]3 4-, N3, CH2-NR6R7 or CH2-OR6;

R3, R3', R4 and R4' are at each occurrence independently OR7, OR8, hydrogen, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or R3 and R4 taken together form a bond, or R3 and R4 taken together with the atoms to which they are attached form a substituted or unsubstituted heterocyclo, or R3 and R3' and/or R4 and R4' taken together with the carbon to which they are attached form C(=O); and R6, R7 and R8 are at each occurrence independently hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or R3 and R4 taken together with the atoms to which they are attached form a substituted or unsubstituted heterocyclo.

In some embodiments, a compound that promotes PTC read-through is represented by Formula VIII:

$$(VIII)$$

wherein:

X represents N, CR8 or the anhydrobase N+R8, wherein R8 represents a hydrogen atom, a hydroxyl or alkyl or methoxy group optionally substituted with a phenyl group, preferably R8 represents a hydrogen atom, R2, R3 and R4 independently represent a hydrogen atom or a halogen atom or an optionally substituted alkyl, amine, alkene, ester, sulfonamide, ether group, such as a methoxy or trifluoromethoxy, or benzyl group, R5 represents a hydrogen atom or an optionally substituted saturated or unsaturated alkyl group, amine, benzyl group, R6 represents an optionally substituted C1-C3 alkyl group, preferably a methyl or ethyl group, and more preferably R6 represents a methyl group, R7 represents a hydrogen atom or an optionally substituted C1-C3 alkyl group and R7 is absent when the ring A is in the b position, and R9 and R10 represent together a carbon bond or independently represent a hydrogen atom, a R11, OR11, SR11, NR11R12 group, wherein R11 and R12 independently represent a hydrogen atom, an oxygen atom, an optionally substituted saturated or unsaturated, C1-C3 alkyl group, which may contain one or more sulfur, oxygen or nitrogen atoms. Preferably, when R11 and/or R12 represent a substituted alkyl group, the alkyl group is substituted with a halogen, preferably fluorine.

In some embodiments, a compound that promotes PTC read-through is represented by Formula IX:

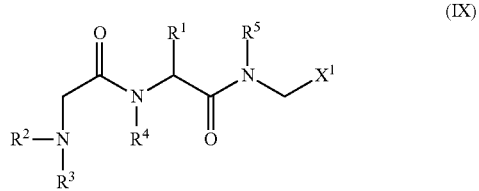

(IX)

wherein R1 represents C1-10 alkyl; R2 and R3 are independently selected from hydrogen atom and C1-10 alkyl which may have a substituent; R4 and R5 are independently selected from hydrogen atom and C1-10 alkyl; X1 represents carboxy, lower alkoxycarbonyl which may have a substituent, carbamoyl which may have a substituent, or hydrazinocarbonyl which may have a substituent.

In some embodiments, a compound that promotes PTC read-through is represented by Formula X:

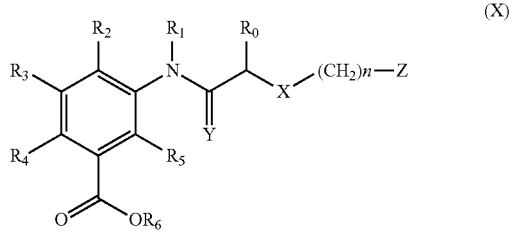

(X)

or pharmaceutically acceptable salts, hydrates, clathrates, prodrugs, polymorphs, stereoisomers, including enantiomers, diastereomers, racemates or mixtures of stereoisomers, thereof wherein:

X is oxygen, sulfur, CO, SO or S(O)2;

Y is oxygen or sulfur;

Z is substituted or unsubstituted aryl, substituted or unsubstituted heteroaryl, substituted or unsubstituted cycloalkyl;

n is an integer from 0 to 4;

R1 is hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, SO2R7, CF3, CN, COOH, COR7, or COOR7;

R0 is hydrogen, or taken together with R1 and the atoms to which they are attached form an optionally substituted 5-7 membered heterocyclic, or heteroaryl ring;

R2, R3, R4 and R5 are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, CF3, OCF3, OCHF2, CN, COOH, COOR7, SO2R7, NO2, NH2N(R7)2;

R6 is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, or any biohydrolyzable group; and each occurrence of R7 is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or CF3;

with the proviso that when X is O, Y is O, n is 0 and R1 is hydrogen, then Z is not 4-chlorophenyl, 4-methylphenyl, 3-chlorophenyl, or 2,4-dichlorophenyl; and with the proviso that when X is O, Y is O, n is 0, R1 is hydrogen, and Z is unsubstituted phenyl at least one of R2-R5 is not hydrogen; and with the proviso that when R3 is COOH, R2, R4, and R5 are not all halogen.

In some embodiments, the following compounds represent compounds that promote PTC read-through:

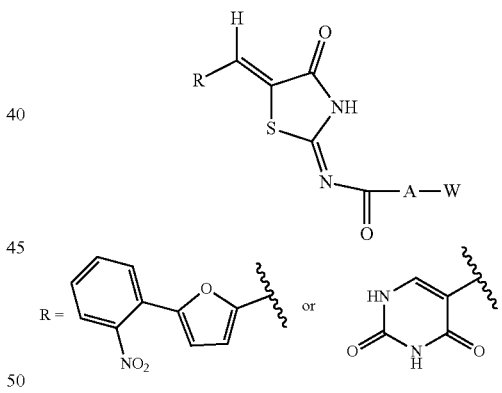

or a pharmaceutically acceptable salt, solvate, polymorph, hydrate, ester, isomer, stereoisomer, or tautomer thereof, wherein:

W is —NRaRb, —C(O)OR4, —C(O)NRaRb, or -HetAr;

A is a bond from C(O) to W, —(CH2)fCH(R1)(CH2)g-, —(CH2)fC(RaRb)(CH2)g-, —(CH2CH2O)h(CH2)t-, —(CH2)t(OCH2CH2)h-, —(CH2)tN(Re)CH2CH2Z, or

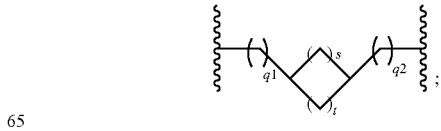

or, in the alternative, A and W combine to form

R1 is —H, —(CH2)nCH3, —CH(CH3)CH2CH3, —CF3, —CH2(Ar), —CH2(HetAr), —CH2S(O)mCH3, —CH2CH2S(O)mCH3, —CH2(CH2)nNReRd, —CH2OH, —CH(CH3)OH, or —(CH2)tCOOH;

R2 is —H, —CH3, —OH, or —CF3;

each of Ra and Rb is independently Re; or, in the alternative, Ra and Rb, together with the nitrogen or carbon atom to which they are attached, combine to form a 4 to 7-membered ring heterocyclic ring which optionally contains additional heteroatoms selected from O, NRg, and S(O)m;

Rc is —H, —CH3, —(CH2)nCH3, —CH(R2)CH3, —CH2-pyridyl, or CH2-imidazolyl;

Rd is —H, —CH3, or —(CH2)nCH3; or, in the alternative, Rc and Rd, together with the nitrogen atom to which they are attached, form a 4-7 membered heterocyclic ring which optionally contains additional heteroatoms selected from O, NRe, and S(O)m;

each Re is independently —H, —(CH2)nCH3, —CH(CH3)2, —CH(CH3)CH2CH3, —(CH2CH2O)pR3, or CH2HetAr; each Rg is independently —H, —(CH2)nCH3, —CH(CH3)2, —CH(CH3)CH2CH3, —(CH2CH2O)pR3, —CH2-phenyl or —CH2-phenyl optionally substituted with F, Cl, —CH3, —OCH3, OCF3, or HetAr;

each R3 is independently —H, —CH3, —OH, or —CF3; alternatively, each R3 is independently —H, —CH3, —CH2CH2-OH, or —CF3;

each R4 is independently —H or —(CH2)nNRcRd;

each HetAr is independently a heteroaryl group optionally selected from pyridyl, pyrimidyl, C-imidazolyl and N-imidazolyl;

D is CH or N;

Q is —O—, —NRa—, —S(O)m-, or —CH—W—;

each k is independently 1, 2, 3 or 4;

each u is independently 1, 2 or 3;

each v is independently 1, 2 or 3;

each p is independently 1 or 2;

each f is independently 0, 1 or 2;

each g is independently 0, 1 or 2;

each h is independently 1 or 2;

each n is independently 0, 1, 2, 3, or 4;

each m is independently 0, 1 or 2;

each of q1 and q2 is independently 0, 1, 2 or 3;

each s is independently 0, 1, 2 or 3; and each t is independently 0, 1, 2 or 3.

In some embodiments, a compound that promotes PTC read-through is represented by Formula XI:

(XI)

or a pharmaceutically acceptable salt, hydrate, clathrate, polymorph, prodrug or stereoisomer thereof wherein:

X is C(=O), C(=S), S, S(=O) or S(O)2;

Y is substituted or unsubstituted alkyl, substituted or unsubstituted aryl, substituted or unsubstituted heteroaryl, substituted or unsubstituted cycloalkyl, substituted or unsubstituted heterocyclo;

R is hydrogen, substituted or unsubstituted alkyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl;

n is an integer ranging from 0-4;

R1 and R2 are each independently hydrogen, substituted or unsubstituted alkyl, substituted or unsubstituted alkenyl, substituted or unsubstituted alkynyl, —(CH2)m-W, carboxyalkyl, alkylcarbonyl, alkyloxyalkyl, alkyloxycarbonyl, arylalkyl, sulfonyl, amide or R1 and R2 together with the atoms to which they are attached form an optionally substituted 5-7 membered heterocyclic, an optionally substituted 5-7 membered heteroaryl ring or R1 and R2 together form:

—C(O)—CH2—, —CH2—C(O)—, —C(O)—CH2—CH2—,
—CH2—CH2—C(O)—, —C(O)—CH2—C(O)—,
—CH2—C(O)—CH2—, —CH2—CH2—, —(CH2)3—,
—CH=CH—;

W is at each occurrence independently hydrogen, halogen, hydroxy, alkoxy, carboxy, aldehyde, NH2, NR14R14' nitro, cycloalkyl, heteroaryl, heteroarylalkyl;

where (i) each occurrence of R" and R14' is independently selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or CF3; or (ii) R14 and R14', together with the nitrogen atom to which they are bonded, join to form an optionally substituted heterocyclic ring containing from 5 to 8 ring atoms of which from 1 to 3 are heteroatoms;

m is an integer ranging from 1-4;

R3-R6 are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., CF3), haloalkoxy (e.g., OCF3 or OCHF2), OH, CN, COOH, COOR15, SO2R15, NO2, NH2, or NR14R14' and R15 is selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or CF3.

In some embodiments, a compound that promotes PTC read-through is represented by Formula XII:

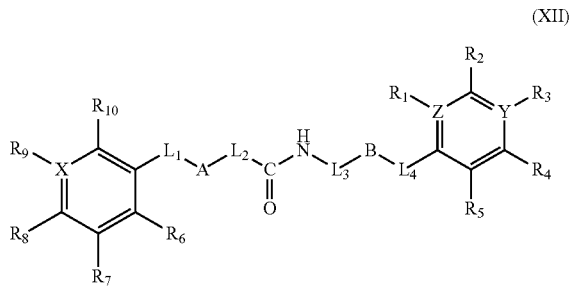

(XII)

a stereoisomer, pharmaceutically acceptable salt, oxide, solvate, or ester thereof, where:

A is selected from the group consisting of: absent; —O—; —CR11═CH—; —S—; —CHR12NH—; —NR13-; substituted or unsubstituted C3-8 cycloalkylene; substituted or unsubstituted arylene; substituted or unsubstituted heterocyclylene; and substituted or unsubstituted heteroarylene where the substituents of A are selected from the group consisting of halogen, OH, CN, NO2, C(O), NH2, H, C1-6 alkyl, C1-6 alkyl substituted with a —COOH, C2-6 alkenyl, C2-6 alkynyl, C4-7 cycloalkylalkyl, and monocyclic aryl;

B is selected from the group consisting of: absent; —O—; —CR14═CH—; —NH—C(O)—; —C(S)—NH—; —N═CH—; substituted or unsubstituted C3-8 cycloalkylene; substituted or unsubstituted arylene; substituted or unsubstituted heterocyclylene; and substituted or unsubstituted heteroarylene where the substituents of B are selected from the group consisting of halogen, OH, CN, NO2, C(O), NH2, H, C1-6 alkyl, C1-6 alkyl substituted with a —COOH, C2-6 alkenyl, C2-6 alkynyl, C4-7 cycloalkylalkyl, and monocyclic aryl;

L1 to L4 are independently selected from the group consisting of: absent; —S0-1-C1-6 alkylene-S0-1-; —S0-1-C2-4 alkenylene-S0-1-; —S0-1-C2-4 alkynylene-S0-1-; and —C(S)—NH—; and —NH—;

X is C or N;

Z is C, O, or S;

Y is C or absent;

R1 is H, C1-6 alkyl, C2-6 alkenyl, C2-6 alkynyl, OR16, C(O)NR17R18, NR19C(O)R20;

R2 is H, C1-6 alkyl, C2-6 alkenyl, C2-6 alkynyl, OR16, NO2, C(O)N17R18, NR19C(O)R20, heterocyclyl or heteroaryl containing 1-5 heteroatoms selected from the group consisting of nitrogen, sulfur, and oxygen;

R3 is H, C1-6 alkyl, C2-6 alkenyl, C2-6 alkynyl, halogen, OR16, C(O)NR17R18, C(O)OR16, NR19C(O)R20;

R4 is H, C1-6 alkyl, C2-6 alkenyl, C2-6 alkynyl, OR16, C(O)OR16, C(O)NR17R18, NR19C(O)R16, heteroaryl containing 1-5 heteroatoms selected from the group consisting of nitrogen, sulfur, and oxygen;

R5 is H, C1-6 alkyl, C2-6 alkenyl, C2-6 alkynyl, halogen, OR16, C(O)OR16;

R6 is H, C1-6 alkyl, C2-6 alkenyl, C2-6 alkynyl, halogen, OR16, NR17R18, heteroaryl or heterocyclyl containing 1-5 heteroatoms selected from the group consisting of nitrogen, sulfur, and oxygen, N═NR15;

R7 is H, C1-6 alkyl, C2-6 alkenyl, C2-6 alkynyl, halogen, OR16, NO2, NR19C(O)R20, S(O)2NR17R18;

R8 is H, C1-6 alkyl, C2-6 alkenyl, C2-6 alkynyl, halogen, OR16, NR19C(O)R20;

R9 is H, C1-6 alkyl, C2-6 alkenyl, C2-6 alkynyl, halogen, NO2, OR16, S(O)2NR21R22;

R10 is H, C1-6 alkyl, C2-6 alkenyl, C2-6 alkynyl, halogen, NR17R18, OR16;

R1 to R10 are each optionally substituted 1 to 3 times with substituents selected from the group consisting of halogen, —OH, —OR21, —C(O)R21, —C(O)OR21, C(O)NR21R22, —NHR21, —NR21R22, —SR21, —S(O)R21, —S(O)2R21, NH2, CN, NO2, C1-6 alkyl, C2-6 alkenyl, C2-6 alkynyl, C3-6 cycloalkyl, C4-7 cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;

R11 is H, C1-6 alkyl, C2-6 alkenyl, C3-6 alkynyl, NR19C(O)R20;

R12 is H, C1-6 alkyl, C2-6 alkenyl, C3-6 alkynyl, C(O)OR16;

R13 is NHNH; R14 is C(O)OR21;

R10 and R12 can combine to form a —NH—C(O)— group;

R13 and R15 can combine to form a —N—N═N— group;

R15 to R22 are independently H, C1-6 alkyl, C2-6 alkenyl, C2-6alkynyl, C3-6 cycloalkyl, C4-7 cycloalkylalky, C1-6 alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each R15 to R22 optionally substituted from 1-3 times with substituents selected from the group consisting of halogen, oxy, OH, CN, NO2, —C(O), NH2, H, C1-6 alkyl, C2-6 alkenyl, C2-6 alkynyl, C3-6 cycloalkyl, C4-7 cycloalkylalkyl, O-aryl substituted with C1-6alkyl, C(O)NHCH2-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—C1-6 alkyl, and a monocyclic aryl;

R21 and R22 can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, NO2, NH2, C1-6 alkyl, C2-6 alkenyl, C2-6 alkynyl, C3-6 cycloalkyl, C4-7 cycloalkylalkyl, a monocyclic aryl, and monocyclic heteroaryl; and a pharmaceutically acceptable carrier.

Other compounds suitable for promoting PTC read-through in for use in the instant invention can be found in U.S. Patent Application Publication Nos. 2015/0274674, 2015/0051251, 2013/0217717, 2012/0087896, 2011/0046136, 2011/0003843, 2010/0093867, 2008/0207538, 2007/0203123, 2006/0166926, and 2006/0167263; International Patent Application Publication Nos. WO 2015/134711, WO 2015/109248, WO 2013/142346, WO 2012/016930, WO 2008/101935, WO 2004/009558, WO 2004/009610, WO 2004/009533, and WO 2014/055644; and U.S. Pat. Nos. 8,163,782 and 6,992,096, the disclosures of each of which are incorporated by reference herein in their entireties.

In some embodiments, the method of treating cancer in a subject includes administering compounds that promote PTC read-through that are disclosed herein in combination with molecules that inhibit at least one immune checkpoint protein disclosed herein. In some embodiments, the method includes administering a therapeutically effective amount of a compound that promotes PTC read-through and a therapeutically effective amount of at least one checkpoint inhibitor.

In some embodiments, the method includes administering compounds that promote PTC read-through in combination with anti-PD-1 antibodies. In some embodiments, the method includes administering compounds that promote PTC read-through in combination with anti-PD-L1 antibodies. In some embodiments, the method includes administering compounds that promote PTC read-through in combination with anti-CTLA-4 antibodies. In some embodiments, the method includes administering compounds that promote PTC read-through in combination with anti-PD-1 and anti-CTLA-4 antibodies. In some embodiments, the method includes administering compounds that promote PTC read-through in combination with anti-PD-L1 and anti-CTLA-4 antibodies.

In some embodiments, the amount of a compound for promoting PTC read-through administered to the individual is included in any of the following ranges: about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, about 250 to about 300 mg/kg, about 300 to about 350 mg/kg, about 350 to about 400 mg/kg, about 400 to about 450 mg/kg, or about 450 to about 500 mg/kg.

In some embodiments, the checkpoint inhibitors are administered at dosages: 0.1 mg/kg, 0.2 mg/kg, 0.3 mg/kg, 0.4 mg/kg, 0.5 mg/kg, 1.3 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 33.3 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg.

In a preferred embodiment, antibodies against PD-1, PD-L1 and CTLA-4 are administered at a dose of 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg. The dose administered may be every day, every 2 days, every 3 days, every 4 days, every 5 days, every week, every 2 weeks, every 3 weeks, every 4 weeks, and so on until there is remission.

In some embodiments, a method for generating an immune response in an individual in need thereof comprising administering to the individual a therapeutically effective amount of a compound that inhibits NMD complex. In some embodiments, a method of treating cancer in a subject includes administering to the individual a therapeutically effective amount of a compound that inhibit NMD complex.

As used herein, the phrase "NMD degradation complex" refers to any one of the intracellular proteins that participates in NMD of an mRNA bearing a PTC (such as, but not limited to, one or more of UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7). As such, the compound inhibits the function of one or more NMD degradation complex proteins, thereby allowing a PTC-bearing mRNA to be translated into a polypeptide.

Candidate compounds can be, without limitation, small molecule chemical compounds (such as any of the small molecules described above), antibodies, proteins, or any combination thereof.

In some embodiments, an inhibitor of NMD complex is a compound of formula XIII:

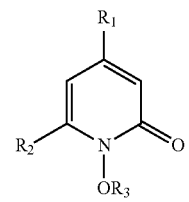

(XIII)

wherein
$R_1$ is $(C_1-C_6)$ alkyl;
$R_2$ is $(C_1-C_{10})$ straight or branched alkyl, $(C_3-C_6)$cycloalkyl or phenoxy$(C_1-C_3)$alkyl, where the phenoxy group is substituted by substituted or unsubstituted phenoxy; and
$R_3$ is hydrogen or a pharmacologically acceptable salt.

In some embodiments, the inhibitor of NMD complex is a compound of the Formula XIV:

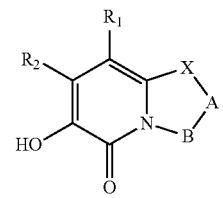

(XIV)

wherein X is N, S, S=O, S(=O)$_2$ or $CR_3R_4$;
A and B are each independently $CR_5R_6$ or taken together are $CR_7$=$CR_8$;
$R_1$, $R_2$, $R_3$, $R_4$, $R_5$, and $R_6$, are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR_9R_9$, amido, or alkoxycarbonyl;
$R_7$ and $R_8$ are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, NR₉R₉', amido, or alkoxycarbonyl; or are taken together to form a substituted or unsubstituted aryl, heterocyclo or heteroaryl ring; and R₉ and R₉' are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or disubstituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, nitro, cyano, carboxy, carbamyl, alkoxycarbonyl, guanidino or heterocyclo alkyl.

Other non-limiting examples of NMD complex inhibitors include:

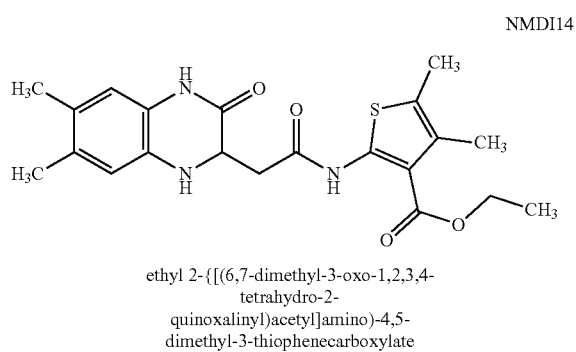

ethyl 2-{[(6,7-dimethyl-3-oxo-1,2,3,4-tetrahydro-2-quinoxalinyl)acetyl]amino}-4,5-dimethyl-3-thiophenecarboxylate

NMDI14

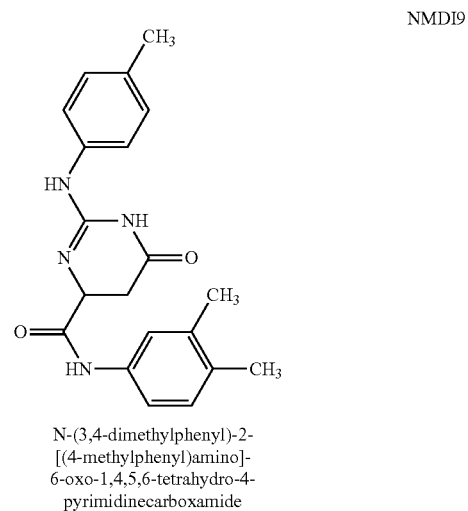

N-(3,4-dimethylphenyl)-2-[(4-methylphenyl)amino]-6-oxo-1,4,5,6-tetrahydro-4-pyrimidinecarboxamide

NMDI9

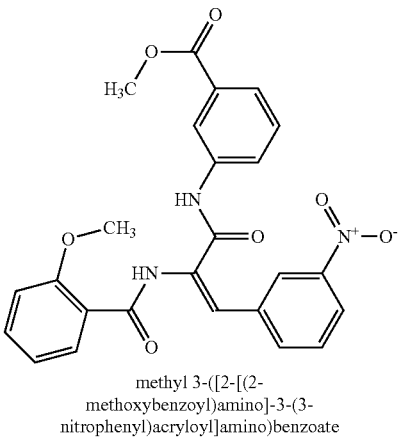

methyl 3-({2-[(2-methoxybenzoyl)amino]-3-(3-nitrophenyl)acryloyl]amino)benzoate

NMDI25

In one embodiment, the compound is not an inhibitory nucleic acid (such as, but not limited to, an antisense oligonucleotide or a small inhibitory RNA (siRNA)). In another embodiment, the compound is any of the compounds disclosed in U.S. Patent Application Publication No. 2013/0224237.

Embodiments of the invention comprise the generation of multi-domain molecules comprising a target specific domain and at least one domain, which modulates expression and function of molecules associated with nonsense mediated decay pathways.

Methods of treating a patient comprise administration of a therapeutically effective amount of multi-domain biologically active molecules. In a preferred embodiment, the multi-domain molecules comprise a cell binding ligand which binds to cells in the tumor stroma (such as, for example, endothelial cells, fibroblasts or immune cells) for specifically targeting an oligonucleotide, e.g. interference RNA (RNAi) to a desired cell in vivo. The cell binding ligands are generated against specific products expressed by a target cell, for example, integrins, glucose-regulated protein 78, neuropilin, growth factor receptors, e.g. VEGF receptors, and the oligonucleotides are specific for inhibiting the nonsense mediated decay pathway and associated molecules. Inhibition of the nonsense mediated decay pathway allows for the up-regulation of existing antigens and/or the induction of new antigens not previously expressed on the target cells and/or novel antigens which results in the induction or enhancement of antigenicity of a the target cell ultimately leading to its destruction by the immune system.

In other embodiments, a composition for inhibiting nonsense mediated decay (NMD) pathways in patients in vivo comprises at least one first domain which specifically binds to at least one tumor cell target or normal cell target in a tumor stroma and at least one second domain specific for a molecular component of nonsense mediated decay pathways, wherein the second domain comprises an antisense oligonucleotide molecule, peptides, proteins, nucleic acids, organic or inorganic molecules, which inhibit the nonsense mediated decay pathway.

In some embodiments, the oligonucleotide molecule of the second domain, comprises at least one of a short interfering RNA (siRNA); a micro-interfering RNA (miRNA); antisense oligonucleotides; a small, temporal RNA (stRNA); a short, hairpin RNA (shRNA), or combinations thereof.

In some embodiments, the oligonucleotide molecule of the second domain, inhibits function and/or expression of at least one factor associated with the NMD pathway comprising at least one of: RENT1, RENT2, eIF4A, UPF1, UPF2, UPF3B, RNPS1, Y14, MAGOH, NMD1, SMG, or combinations thereof.

In some embodiments, the first domain specifically or selectively binds to any target desired. Preferably, the target is a tumor cell target, a normal cell target, cells in tumor stroma or combinations thereof. Preferably, the first domain specifically binds to tumor or normal cell targets comprising: vascular endothelial growth factor (VEGF), vascular endothelial growth factor receptor (VEGFR-2), Tie2; fibronectin, vitronectin, collagen, laminin, fibroblast antigens, fibroblast activation protein (FAP), glucose-regulated protein 78 (GRP78), stromal derived factor 1 (SDF-1), MCP-1, MIP-1α, MIP-1β, RANTES, exotaxin IL-8, C3a, P-selectin, E-selectin, LFA-1, VLA-4, VLA-5, CD44, MMP activation, VEGF, EGF, PDGF, VCAM, ECAM, G-CSF, GM-CSF, SCF, EPO, tenascin, neurophilin, MAdCAM-1, neuropilin-1, α4 integrins, α5 integrins, or beta defensins 3 and 4.

In some aspects, the compound that binds (such as preferentially binds) to one or more NMD degradation complex proteins (such as, but not limited to, UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7) is an antibody. In some embodiments, the antibodies are NMD degradation complex protein antagonists and can inhibit NMD.

Variants of antibodies can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Nucleic acid molecules encoding amino acid sequence variants of the antibody can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In some aspects, the compound that binds (such as preferentially binds) to one or more NMD degradation complex proteins (such as, but not limited to, UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7) is a non-antibody binding polypeptide. In some embodiments, the non-antibody binding polypeptide is a NMD degradation complex protein antagonist and can inhibit NMD.

Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding to a target, such as any component of the NMD degradation complex discussed herein.

In some embodiments, the method of treating cancer in a subject includes administering compounds that inhibit NMD complex that are disclosed herein in combination with molecules that inhibit at least one immune checkpoint protein disclosed herein. In some embodiments, the method includes administering a therapeutically effective amount of a NMD complex inhibitor and a therapeutically effective amount of at least one checkpoint inhibitor.

In some embodiments, the method includes administering compounds that inhibit NMD complex in combination with anti-PD-1 antibodies. In some embodiments, the method includes administering compounds that inhibit NMD complex in combination with anti-PD-L1 antibodies. In some embodiments, the method includes administering compounds that inhibit NMD complex in combination with anti-CTLA-4 antibodies. In some embodiments, the method includes administering compounds that inhibit NMD complex in combination with anti-PD-1 and anti-CTLA-4 antibodies. In some embodiments, the method includes administering compounds that inhibit NMD complex in combination with anti-PD-L1 and anti-CTLA-4 antibodies.

In some embodiments, the amount of a compound that inhibit NMD complex that is administered to the individual is included in any of the following ranges: about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, about 250 to about 300 mg/kg, about 300 to about 350 mg/kg, about 350 to about 400 mg/kg, about 400 to about 450 mg/kg, or about 450 to about 500 mg/kg.

In some embodiments, the checkpoint inhibitors are administered at dosages: 0.1 mg/kg, 0.2 mg/kg, 0.3 mg/kg, 0.4 mg/kg, 0.5 mg/kg, 1.3 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 33.3 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg.

In a preferred embodiment, antibodies against PD-1, PD-L1 and CTLA-4 are administered at a dose of 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg. The dose administered may be every day, every 2 days, every 3 days, every 4 days, every 5 days, every week, every 2 weeks, every 3 weeks, every 4 weeks, and so on until there is remission.

In some embodiments, a method of treating a subject with cancer may comprise administering a therapeutically effective amount of a compound that promotes PTC read-through. In some embodiments, a method of treating a subject with cancer may comprise administering a therapeutically effective amount of a compound that inhibits NMD complex. In some embodiments, a method of treating a subject with cancer may comprise administering a combination of a compound that promotes PTC read-through and a compound that inhibits NMD complex. In some embodiments, a method of treating a subject with cancer may comprise administering a combination of a compound that promotes PTC read-through and a compound that inhibits NMD complex, and further administering at least one checkpoint inhibitor disclosed herein.

In some aspects, provided herein are methods for generating an immune response in an individual in need thereof and/or methods inducing the expression of one or more neoantigens on the surface of an abnormal cell. NMD is an evolutionary conserved mRNA surveillance pathway in eukaryotic cells that detects and eliminates mRNAs harboring premature termination codons (PTCs). Without wishing to be bound by theory, upregulation of gene expression when NMD is inhibited in tumor cells will translate into a therapeutically useful enhancement of tumor antigenicity, namely that the new products will function as effective tumor antigens, capable of eliciting an immune response which will contribute to tumor rejection. Inhibition will be accomplished by administering an effective amount of one or both of the compounds for promoting PTC read-through and inhibition of the NMD degradation complex described above to an individual in need thereof. In one embodiment, the protein translated from the mRNA following PTC read-through and inhibition of the NMD degradation complex is a non-functional protein. An effective amount can result in the functionality as described below and herein.

In some embodiments, the amount of a compound for promoting PTC read-through and the amount of compound for inhibiting NMD complex administered to the individual is included in any of the following ranges: about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, about 250 to about 300 mg/kg, about 300 to about 350 mg/kg, about 350 to about 400 mg/kg, about 400 to about 450 mg/kg, or about 450 to about 500 mg/kg. In some embodiments, the amount of a telomerase inhibitor in the therapeutically effective amount administered to the individual (e.g., a unit dosage form) is in the range of about 5 mg to about 500 mg, such as about 30 mg to about 300 mg or about 50 mg to about 200 mg or about 10 mg to about 100 mg.

In some embodiments, the checkpoint inhibitors are administered at dosages: 0.1 mg/kg, 0.2 mg/kg, 0.3 mg/kg, 0.4 mg/kg, 0.5 mg/kg, 1.3 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 33.3 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg.

In a preferred embodiment, antibodies against PD-1, PD-L1 and CTLA-4 are administered at a dose of 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg. The dose administered may be every day, every 2 days, every 3 days, every 4 days, every 5 days, every week, every 2 weeks, every 3 weeks, every 4 weeks, and so on until there is remission.

In further embodiments, treatment with one or more compounds including amlexanox, PTC read-through compounds, NMD complex inhibitors, and checkpoint inhibitors, or combination thereof according to any of the methods disclosed herein results in at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decrease in tumor size when compared to tumors that are not treated with the compounds disclosed herein.

In some embodiments treatment with one or more compounds including amlexanox, PTC read-through compounds, NMD complex inhibitors, and checkpoint inhibitors, or a combination thereof according to any of the methods disclosed herein exhibit at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% any of CD4+, CD8+, CD3+, and/or CD45+ effector T cell responses (e.g. intratumoral T-cell infiltration) when compared to T-cell responses in tumors that are not treated with the compounds disclosed herein.

In one embodiment the PTC read-through inhibitor is Ataluren (PTC124) and the compound that inhibits nonsense-mediated decay is NMDI14. In another embodiment, the PTC read-through inhibitor (e.g., Ataluren) and the compound that inhibits nonsense-mediated decay (e.g., NMDI14) is administered in combination with an antibody to PD-1. In another embodiment, the PTC read-through inhibitor (e.g., Ataluren) and the compound that inhibits nonsense-mediated decay (e.g., NMDI14) is administered in combination with an antibody to CTLA-4. In a further embodiment, the combination of a PTC read-through inhibitor (e.g., Ataluren) and the compound that inhibits nonsense-mediated decay (e.g., NMDI14) and a single compound that inhibits an immune checkpoint protein (e.g., an anti-PD-1 antibody or an anti-CTLA-4 antibody) is as effective or more effective in inhibiting tumor growth as compared to a combination of two or more compounds that inhibit an immune checkpoint protein (e.g., a combination of an anti-PD-1 antibody and an anti-CTLA-4 antibody) alone.

Epigenetic Modulatory Compounds

In some embodiments of any of the methods disclosed herein, the method further comprises administration of one or more epigenetic modulatory compounds. As used herein, "epigenetic" is intended to refer to the physical changes that are imposed in a cell upon chromosomes and genes wherein the changes affect the functions of the DNA and genes in the chromosomes and which do not alter the nucleotide sequence of the DNA in the genes. Representative examples of epigenetic modulations include, but are not limited to, covalent chemical modifications of DNA such as methylation and acetylation as well as non-covalent and non-chemical modifications of DNA-DNA super-coiling and association with chromosomal proteins like histones. Representative, non-limiting examples of the results of epigenetic changes include increasing or decreasing the levels of RNAs, and thereby protein products, produced by certain genes and/or changing the way that transcription factors bind at to gene promoters.

Suitable epigenetic modulatory compounds for use in the methods of the present invention include, without limitation, one or more of histone deacetylase (HDAC) inhibitors, azocytidine, BET inhibitors, EZH2 inhibitors, and/or dotIL. In some embodiments, the epigenetic modulatory compounds are one or more of vorinostat (Merck), romidepsin (Celgene), decitabine (Otsuka); and 5-azocytidine (Celgene), panobinostat (Novartis), or belinostat (Spectrum).

Cancer Treatment

The methods of the present invention may be practiced in an adjuvant setting. "Adjuvant setting" refers to a clinical setting in which an individual has a history of a proliferative disease, particularly cancer, and generally (but not necessarily) has been treated with therapy, which includes, but is not limited to, surgery, radiotherapy, and/or chemotherapy. However, because of a history of the proliferative disease, these individuals are considered at risk of developing that disease, or may harbor detectable and/or microscopic disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy.

In some aspects, any of the methods described herein include the administration of a therapeutically effective amount of an anti-cancer therapy to individuals in need thereof. As used herein, a "therapeutically effective amount" or "therapeutically effective dosage" of an anticancer therapy is an amount sufficient to effect beneficial or desired results. For therapeutic use, beneficial or desired results include clinical results such as decreasing one or more symptoms resulting from cancer, increasing the quality of life of those suffering from cancer, decreasing the dose of other medications required to treat the cancer, enhancing effect of another medication such as via targeting, delaying the progression of the disease, and/or prolonging survival. An effective dosage can be administered in one or more administrations. For purposes of this invention, an effective dosage of an anti-cancer therapy is an amount sufficient to accomplish therapeutic treatment either directly or indirectly. As is understood in the clinical context, a therapeutically effective dosage of an anti-cancer therapy may or may not be achieved in conjunction with another anti-cancer therapy.

In some aspects, any of the methods of treatment described herein can further comprise administering one or more additional anti-cancer therapies to the individual. Various classes of anti-cancer agents can be used. Non-limiting examples include: radiation therapy, alkylating agents (e.g. cisplatin, carboplatin, or oxaliplatin), antimetabolites (e.g., azathioprine or mercaptopurine), anthracyclines, plant alkaloids (including, e.g. vinca alkaloids (such as, vincristine, vinblastine, vinorelbine, or vindesine) and taxanes (such as, paclitaxel, taxol, or docetaxel)), topoisomerase inhibitors (e.g., camptothecins, irinotecan, topotecan, amsacrine, etoposide, etoposide phosphate, or teniposide), podophyllotoxin (and derivatives thereof, such as etoposide and teniposide), antibodies (e.g., monoclonal or polyclonal), tyrosine kinase inhibitors (e.g., imatinib mesylate (Gleevec® or Glivec®)), hormone treatments, soluble receptors and other antineoplastics (e.g., dactinomycin, doxorubicin, epirubicin, bleomycin, mechlorethamine, cyclophosphamide, chlorambucil, or ifosfamide).

T Cell Agonists

In some embodiments of any of the methods disclosed herein, the method further comprises administration of one or more compounds that activate T cells. These are usually agonist antibodies, often directed to immune co-stimulatory molecules, such as members of the tumor necrosis factor (TNF) receptor superfamily and the B7-CD28 superfamily. Non-limiting examples of T cell agonists appropriate for use in the present invention include, without limitation, activators of CD27 (e.g. CDX-1127 (Celldex Therapeutics)), GITR, B7-H3, CD28 (e.g. TGN1412), CD40, interleukin-2 receptor subunit beta (ILR2P; a.k.a. CD122; e.g., NKTR-214), CD137 (a.k.a. TNFRSF9, 4-1BB, and induced by lymphocyte activation (ILA)), ICOS, and/or OX40 (a.k.a. CD134 and TNFRSF4; e.g., MED10562, MED16469 and MED16383 (AstraZeneca)). In some embodiments, the immune co-stimulatory molecules can also be Ig fusion proteins, such as OX40-IgG.

Molecular Adjuvants

In some embodiments of any of the methods disclosed herein, the method further comprises administration of one or more molecular adjuvants. As used herein, "molecular adjuvant" refers to molecules that enhance the immune response which include, without limitation, agents that activate dendritic cells. Molecular adjuvants can include, without limitation, proteins, lipids, nucleic acids, carbohydrates, or chemical compounds for which dendritic cells have a receptor whose occupancy leads to an intracellular signal transduction and a change in the antigen presenting cell phenotype, resulting in an improvement in the quantity or quality of the ensuing immune response. Non-limiting examples of molecular adjuvants include agonists of TNF receptor superfamily, Toll-like receptor (TLR) ligands, and intracellular DNA sensor agonists.

TNFR Agonists as Molecular Adjuvants

The TNFR superfamily includes many important receptors on dendritic cells, macrophages, and T cells. For example, cluster of differentiation 40, (CD40) is a costimulatory protein found on antigen presenting cells and is required for their activation. The binding of CD 154 (CD40L) on TH cells to CD40 activates antigen presenting cells and induces a variety of downstream effects. CD40L strongly up-regulates the expression of CD80 and CD86 on DCs and causes CD4+ T cells to differentiate toward Th1 cells.

Other TNFR agonists that have been shown to have significant potential as molecular adjuvants include, without limitation, 4-1BB, CD30, herpes virus entry mediator, CD40, CD27, OX40, and glucocorticoid-induced TNFR-related protein (GITR), whose ligands are 4-1BBL, CD30L, LIGHT, CD27L/CD70, GITRL, and ICOS.

TLR Agonists

The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-IR) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR-1/2 agonist; CFA, a TLR-2 agonist; MALP2, a TLR-2 agonist; Pam2Cys, a TLR-2 agonist; FSL-1, a TLR-2 agonist; Hib-OMPC, a TLR-2 agonist; polyribosinic:polyribocytidic acid (Poly I:C), a TLR-3 agonist; polyadenosine-polyuridylic acid (poly AU), a TLR-3 agonist; Polyinosinic-Polycytidylic acid stabilized with poly-L-lysine and carboxymethylcellulose (Hiltonol®), a TLR-3 agonist; monophosphoryl lipid A (MPL), a TLR-4 agonist; LPS, a TLR-4 agonist; bacterial flagellin, a TLR-5 agonist; sialyl-Tn (STn), a carbohydrate associated with the MUC1 mucin on a number of human cancer cells and a TLR-4 agonist; imiquimod, a TLR-7 agonist; resiquimod, a TLR-7/8 agonist; loxoribine, a TLR-7/8 agonist; and unmethylated CpG dinucleotide (CpG-ODN), a TLR-9 agonist.

Intracellular DNA Sensor Agonists

The cGAS-STING pathway is a component of the innate immune system that functions to detect the presence of cytosolic DNA and, in response, trigger expression of inflammatory genes. DNA is normally found in the nucleus of the cell. Localization of DNA to the cytosol is associated with tumorigenesis or viral infection. The cGAS-STING pathway acts to detect cytosolic DNA and induce an immune response.

Upon binding DNA, the protein cyclic GMP-AMP Synthase (cGAS) triggers dimerization of AMP and GMP to form cyclic GMP-AMP (cGAMP). cGAMP and other cyclic dinucleotides binds to Stimulator of Interferon Genes (STING) which triggers TBK1 to phosphorylate downstream transcription factors IRF3, which induces the type 1 IFN response, and STAT6, which induces chemokines such as CCL2 and CCL20 independently of IRF3 (Burdette et al., 2011, Nature 478, 515-18). The signaling pathways activated by STING combine to induce an innate immune response to cells with ectopic DNA in the cytosol. Loss of STING activity inhibits the ability of mouse embryonic fibroblasts to fight against infection by certain viruses, and more generally, is required for the type 1 IFN response to introduced cytosolic DNA.

DNA has been shown to be a potent adjuvant to boost the immune response to antigens encoded by vaccines. cGAMP, through IRF3 activation of STING, stimulates transcription of interferon. This makes cGAMP a potential vaccine adjuvant capable of boosting inflammatory responses. Studies have shown that vaccines encoded with the chicken antigen, ovalbumin (OVA), in conjunction with cGAMP, were able to activate antigen-specific T and B cells in a STING-dependent manner in vivo. When stimulated with OVA peptide, the T cells from mice vaccinated with OVA+cGAMP were shown to have elevated IFN-g and IL-2 when compared to animals receiving only OVA. Furthermore, the enhanced stability of cGAMP, due to the unique 2'-5' phosphodiester bond, may make it a preferred adjuvant to DNA for in vivo applications.

Micro Environment Modulators

In other embodiments of any of the methods disclosed herein, the method further comprises administration of one or more microenvironment modulators. "Microenvironment modulators" refer to factors capable of generating an immunosuppressive tumor microenvironment that supports tumor growth. One such modulator is indoleamine (2,3)-dioxygenase (IDO) which was also identified as a checkpoint protein (see supra). IDO is an enzyme with two isoforms (IDO1 and IDO2) that acts at the first step in the metabolic pathway that breaks down the essential amino acid tryptophan. IDO exerts its immunomodulatory effects by shutting down the effector T cells of the immune system. IDO expression also directly activates the regulatory T cells, a subset of T cells whose major function is to shut down T cell-mediated immunity at the end of an immune reaction.

Another microenvironment modulator is tryptophan 2,3-dioxygenase (TDO). TDO plays a central role in the physiological regulation of tryptophan flux in the human body. It catalyzes the first and rate limiting step of tryptophan degradation along the kynurenine pathway thereby regulating systemic tryptophan levels. It has been shown that tryptophan 2,3-dioxygenase is expressed in a significant proportion of human tumors. In the same study, tryptophan 2,3-dioxygenase expression by tumors prevented their rejection by immunized mice. A tryptophan 2,3-dioxygenase inhibitor developed by the group restored the ability of these mice to reject tryptophan 2,3-dioxygenase-expressed tumors, demonstrating that tryptophan 2,3-dioxygenase inhibitors display potential in cancer therapy.

Other microenvironment modulators suitable for use in the methods of the present invention can include, without limitation, IDO, TDO, CD73, COX2 inhibitors, CD39 inhibitors, and A2A receptor agonists, and antibodies to CD73, CD39, and A2A receptors.

Chemokine Receptor Antagonists

In yet other embodiments of any of the methods disclosed herein, the method further comprises administration of one or more chemokine receptor antagonists. Chemokine receptors are G protein-coupled receptors containing seven transmembrane domains that are found predominantly on the surface of leukocytes. Chemokine receptors are divided into different families: CXC chemokine receptors, CC chemokine receptors, CX3C chemokine receptors and XC chemokine receptors corresponding to the four distinct subfamilies of chemokines they bind.

In some embodiments, the methods of the present invention include one or more antagonists to a chemokine receptor of the CXC chemokine receptor family. Suitable CXC family member targets include CXCR1 (a.k.a. IL8RA or CD181), which is thought to have a role in the cell growth and angiogenesis required for tumor survival and CXCR4 (a.k.a. fusin or CD 184).

In other embodiments, the methods of the present invention include one or more antagonists to a chemokine receptor of the CC chemokine receptor (or beta chemokine receptor) family which can include, without limitation, CCR2, CCR5, and/or CCR4.

Cytokine Therapies

In other embodiments of any of the methods disclosed herein, the method further comprises administration of one or more cytokine therapies. Cytokines are a broad group of proteins produced by many types of cells present within tumors which have the ability to modulate immune responses. These immune-modulating effects allow them to be used as drugs to provoke an immune response. Two commonly used groups of cytokines are interferons and interleukins Non-limiting examples of cytokine therapies appropriate for use in the present invention include, without limitation, Type I IFN (IFNα), IL-2, IL-7, IL-15, IFNγ, IL-10, IL-12, IL-21, IL-33, IL-35, FLT3, and/or anti-TGFβ. The receptors for these proteins (e.g., IL-2R, IL-7R, IL-15R, IL-10R, IL-12R, or IL-21R, etc.) can also be targeted (e.g., with an activating drug (e.g. small molecule), antibody, or polypeptide).

Other Immunotherapies

Other immunotherapies appropriate for use with the methods disclosed herein include, without limitation, immunogenic chemotherapy, XRT, oncolytic viruses, cryotherapy, TACE, intratumoral injection of immunomodulatory agents, targeted therapies for oncogenic pathways (MAPK, beta catenin, PI3K/PTEN, FGFR3, etc.), epigenetic therapy, CSF1/CSFR1 depleting antibodies and anti-CCR4 (e.g., mogamulizumab; Kyowa), anti-IL-8/IL-8R, anti-CCR2, anti-CCR5, anti-CXCR1/CXCR2, anti-CTLA4, anti-CCR4, anti-CCR8, anti-CD25, anti-KIR, anti-NKG2a, anti-NKG2DL (MICA), arginase, IDO/TDO, adenosine, A2AR, CD39, CD73, PI3K gamma, anti-NKG2D, CD94 as well as therapies for activating or inhibiting one or more of CD47/SIRPa, Mer/Axl/Tyro3, TIM3, MFG-E8/GAS6, and/or DD1alpha.

In some embodiments, the methods disclosed herein can be used in combination with any CAR-T therapy known in the art. Chimeric antigen receptors (CARs, also known as chimeric T cell receptors) are synthetic constructs that are designed to be expressed in host T cells or NK cells and to induce an immune response against a specific target antigen and cells expressing that antigen. The CAR typically comprises an extracellular domain, a transmembrane domain, and an intracellular domain. The extracellular domain is usually an antibody fragment, such as a scFv or Fab fragment, that can be targeted to bind to any antigen. The transmembrane domain can be derived from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 or CD154. The intracellular domain are usually selective T-cell activating moieties, including the endodomains of CD3-ζ, CD28, ICOS, CTLA4, PD1, PTLA, HVEM, CD27, 4-1BB, OX40, DR3, DcR3, FAS (CD95), GITR, CD30, CD40, SLAM, CD2, 2B4, TIM1, TIM2, TIM3, TIM4, TNFR1 (CD120a), TNFR2 (CD120b), LTβR, Ly108, CD84, Ly9, CRACC, BTN1, BTN2, BTN3, TIGIT, CD226, CRTAM (CD355), CD96, CD160, LAG3, LAIR1, B7-1, RANK (CD265), TACI, BAFFR, BCMA, TWEAKR, EDAR, XEDAR, RELT, DR6, TROY, NGFR, OPG, TRAILR1-4 and B7-H1. Various combinations of an extracellular domain, a transmembrane domain, and an intracellular domain can be used in constructing a CAR.

In some embodiments, the methods disclosed herein can be used in combination with any adoptive cell transfer (ACT) therapy. ACT is a very effective form of immunotherapy and involves the transfer of immune cells with antitumor activity into cancer patients. ACT involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). They can also be derived or from blood if they are genetically engineered to express antitumor T cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Pharmaceutical Compositions

Also provided herein are pharmaceutical compositions comprising any of the compounds disclosed herein, including amlexanox, PTC read-through compounds, NMD complex inhibitors, and checkpoint inhibitors. The pharmaceutical compositions of the invention may include one or more of tablets, capsules, granules, powder, pellets, caplets, minitablets, lozenges, capsule filled with minitablets and/or pellets, multi-layer tablets, granules for suspension, granules or powder filled in a sachet. In other embodiments, the composition of the present invention can be coated to give film-coated tablets.

The composition of the invention may be prepared by mixing pharmaceutically excipients and granulating them with aqueous or alcoholic solution of compounds along with sugars optionally with other pharmaceutically acceptable excipients. The granules may be dried and lubricated and converted into a suitable dosage form.

The stable solid pharmaceutical compositions of compounds, such as amlexanox, PTC read-through compounds, NMD complex inhibitors, and checkpoint inhibitors may be prepared by processes known to a person having ordinary skill in the art of pharmaceutical technology such as direct compression, wet or dry granulation, slugging, hot melt granulation, hot melt extrusion, fluidized bed granulation, extrusion-spheronization, spray drying and solvent evaporation. In an embodiment, the stable composition of compounds that promote PTC read-through and compounds that inhibit the NMD complex or pharmaceutically acceptable salts thereof are prepared by dry/wet granulating the compound(s) with one or more sugars and one of more pharmaceutically acceptable excipients, and optionally mixing the granules with other excipients.

Pharmaceutically acceptable excipients may include one or more binders, fillers, lubricants, solubilizers, stabilizers, disintegrants, glidants, and the like.

Suitable "diluents" may include one or more of lactose, microcrystalline cellulose, calcium phosphate, dextrin, dextrose, dextrates, mannitol, sorbitol, sucrose, and the like. In particular, the diluents are lactose and microcrystalline cellulose. The diluent may be present in the extragranular and/or intragranular portions of the composition.

Suitable "disintegrants" may include one or more of crospovidone (polyplasdone), low substituted hydroxypropyl cellulose, carmellose, sodium carboxystarch, calcium carmellose, cornstarch, partially-alphatized starch, sodium croscarmellose, sodium starch glycolate, and the like. In particular, the disintegrant is crospovidone. The disintegrant may be present in extragranular and/or intragranular portion of the composition.

Suitable "binders" may include one or more of hydroxypropyl cellulose, hydroxypropylmethyl cellulose, polyvinyl pyrrolidone (povidone K30), polyvinyl alcohol, partial saponificates of these, starch, and the like. In particular, the binder is polyvinyl pyrrolidone.

Suitable "solubilizers" may include one or more of poloxamer, polyethylene glycols, polysorbates, sodium lauryl sulfate, glyceryl monostearate, glyceryl monooleate, lecithin, polyoxythylene alkyl esters, polyoxyethylene castor oil derivatives, polyoxyethylene fatty acid esters, and the like. In particular, the solubilizers are poloxamer and glyceryl monooleate.

Suitable "stabilizers" may include one or more of citric acid, tartaric acid, fumaric acid, maleic acid, vitamin E acetate and the like. In particular, the stabilizer is vitamin E acetate.

Suitable "lubricants/glidants" includes one or more of magnesium stearate, stearic acid, palmitic acid, calcium stearate, zinc stearate, sodium stearyl fumarate, glyceryl behenate, talc, and the like.

Any of the compounds according to the present invention may be formulated in conventional manner using one or more pharmaceutically acceptable carriers or excipients. In some embodiments, multiple routes of administration can be used for drug administration in a given treatment regimen. For example, a compound for promoting PTC read-through can be administered orally while a compound for inhibiting NMD can be administered intravenously. Thus, the compound for use according to the invention may for example be formulated for one or more of oral, sub-lingual, buccal, parenteral, rectal, vaginal, or intranasal administration or in a form suitable for administration by inhalation or insufflation (either through the mouth or nose) or in a form suitable for topical administration, preferably for local application in the eye. In another embodiment, the compound is formulated for topical or subcutaneous administration.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds, such as amlexanox, PTC read-through compounds, NMD complex inhibitors, and checkpoint inhibitors may be formulated for parenteral administration by injection, conveniently intravenous, intramuscular, intratumoral, or subcutaneous injection, for example by bolus injection or continuous intravenous infusion. Formulations for injection may be presented in unit dosage form e.g. in ampoules or in multi-dose containers, optionally with an added preservative. The compositions for parenteral administration may take such forms as suspensions, solutions or emulsions in oily or aqueous vehicles, and may contain formulatory agents such as suspending, stabilizing and/or dispersing agents. Alternatively, the active ingredient may be in dry form such as a powder, crystalline or freeze-dried solid for constitution with a suitable vehicle, e.g. sterile pyrogen-free water or isotonic saline before use. They may be presented, for example, in sterile ampoules or vials.

The compounds may also be formulated in rectal compositions such as suppositories or retention enemas, e.g. containing conventional suppository bases such as cocoa butter or other glyceride.

Tablets for sub-lingual administration may be formulated in a conventional manner.

For intranasal administration the compounds may be used, for example, as a liquid in the form of, for example, a solution, suspension or emulsion, presented in the form of a spray or drops, or as a powder. Preferably the preparation for intranasal administration is delivered in the form of a spray or aerosol from an insufflator or from a pressurized pack or nebulizer with the use of a suitable propellant.

For administration by inhalation the compounds can be conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For topical administration the pharmaceutical compositions may be liquids, for example solutions, suspensions or emulsions (such as nanoparticle- or liposome-containing emulsions) presented in the form of creams, gels, lotions, foams or drops suitable for local application to the eye.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The invention can be further understood by reference to the following examples, which are provided by way of illustration and are not meant to be limiting.

EXAMPLES

Example 1: In Vivo Studies Using PTC Read-Through Compounds, NMD Inhibitors, and Checkpoint Inhibitors Materials and Methods Animals: Female 6-8 week old (estimated age at inoculation) C57BL/6 mice were obtained from Shanghai Lingchang Bio-Technology Co. Ltd (LC, Shanghai, China). The animals were housed at 20-26° C. with a 12 hours light and 12 hours darkness cycle.

Cell Culture: MC38 tumor cells were maintained in vitro as a monolayer culture in DMEM medium supplemented with 10% fetal bovine serum at 37° C. in an atmosphere of 5% CO2 in air. The tumor cells were routinely subcultured twice weekly. Cells in an exponential growth phase were harvested and counted for tumor inoculation.

Therapeutic compounds: Anti-PD-1 and anti-CTLA-4 antibodies were obtained from BioXCell as was an anti-CD8 antibody. The nonsense mediated decay inhibitor NMDI14 (4,5-Dimethyl-2-[[2-(1,2,3,4-tetrahydro-6,7-dimethyl-3-oxo-2-quinoxalinyl)acetyl]amino]-3-thiophenecarboxylic acid ethyl ester, Ethyl 2-{[(6,7-dimethyl-3-oxo-1,2,3,4-tetrahydro-2-quinoxalinyl)acetyl]amino}-4,5-dimethyl-3-thiophenecarboxylate) was obtained from ChemBridge Corp. (La Jolla, Calif.). The RTC Ataluren (PTC124) was obtained from Selleck Chemicals (Houston, Tex.). Compounds were formulated as shown in Table 2.

TABLE 2

Therapeutic compound formulations.

| Compounds | Package | Preparation | Concentration (mg/ml) | Storage |
|---|---|---|---|---|
| Vehicle 1 20% Cremophor-EL +75% saline | — | 4 ml Cremophor-EL added with 15 ml saline. Vortex and sonicates to make 19 ml vehicle 1 for each use. | 0 | 4° C. |
| Vehicle2 20% Cremophor-EL +75% saline | — | 10 g HP-β-CD be measured, 50 ml PBS added. Vortex and sonicated to make Vehicle 2. | 0 | 4° C. |
| NMDI14 | 200 mg/vial | 10 mg Compound C will be measured, 1 ml DMSO will be added. Vortex and sonicate to make stock solution 1. | Stock solution 1 | 4° C. |
|  |  | Vehicle: 5% DMSO +20% Cremophor-EL +75% saline Mix 1 ml stock solution 1 with 19 ml vehicle 1 to make 20 ml dosing solution. | 0.5 | 4° C. |
| PTC124 | 800 mg/vial | 40 mg PTC124 measured, 0.4 ml DMSO will be added. Vortex and sonicate to make stock solution 2. | Stock solution 2 | 4° C. |
|  |  | Vehicle: 2% DMSO +98% (20% HP-β-CD PBS buffer) Dilute 0.4 ml stock solution2 with 19.6 ml 20% HP-β-CD PBS buffer. Vortex and sonicate to make 20 ml dosing solution for each use. | 2 | 4° C. |
| Anti-PD-1 | 8.12 mg/ml | Dilute 1.478 ml 8.12 mg/ml Anti-PD1 antibody solution with 10.523 ml PBS make 12.001 ml dosing solution for each use. | 1 | Immediate use |
| Anti-CTLA-4 | 7.62 mg/ml | Dilute 1.575 ml 7.62 mg/ml CTLA-4 antibody solution with 10.426 ml PBS make 12.001 ml dosing solution for each use. | 1 | Immediate use |

TABLE 2-continued

Therapeutic compound formulations.

| Compounds | Package | Preparation | Concentration (mg/ml) | Storage |
|---|---|---|---|---|
| Anti-CD8 | | Dilute 0.698 ml 5.73 mg/ml anti-CD8 antibody solution with 3.302 ml PBS make 4 ml dosing solution for each use. | 1 | Immediate use |

Tumor Inoculation: Each mouse was inoculated subcutaneously at the right lower flank region with MC38 tumor cells ($1\times10^6$) in 0.1 mL of PBS for tumor development. The treatments were started when the mean tumor size reaches approximately 50 mm$^3$. Compounds were administered and the animal numbers in each study group are shown in Table 2. The date of tumor cell inoculation was denoted as day 0.

Group assignment: Before grouping and treatment, all animals were weighed and the tumor volumes measured using a caliper. Tumor volume was used as numeric parameter to randomize selected animals into specified groups in order to minimize systematic error. The grouping was performed by using StudyDirector™ software (Studylog Systems, Inc. CA, USA). One optimal randomization design (generated by Matched distribution) showing minimal group to group variation in tumor volume was selected for group allocation.

TABLE 3

Administration of the test articles and the animal numbers in each study group

| Group | N | Treatment | Dose (mg/kg) | Dosing Route | Schedule |
|---|---|---|---|---|---|
| 1 | 8 | Vehicle(PBS) | | i.p. | QD × 3 weeks |
| 2 | 8 | PTC124 | 20 | i.p. | QD × 3 weeks |
| 3 | 8 | Anti-PD-1 | 5 10 | i.p. | BIW × 3 weeks |
| 4 | 8 | Anti-CTLA-4 | 10 | i.p. | BIW × 3 weeks |
| 5 | 8 | Anti-PD-1 | 10 10 | i.p. | BIW × 3 weeks |
| 6 | 8 | NMDI14 | 5 20 10 | i.p. | QD × 3 weeks BIW × 3 weeks |
| 7 | 8 | NMDI14 PTC124 Anti-CTLA-4 | 5 20 10 | i.p | QD × 3 weeks BIW × 3 weeks |

TABLE 3-continued

Administration of the test articles and the animal numbers in each study group

| Group | N | Treatment | Dose (mg/kg) | Dosing Route | Schedule |
|---|---|---|---|---|---|
| 8 | 8 | NMDI14 PTC124 Anti-PD-1 | 5 20 10 | i.p | QD × 3 weeks BIW × 3 weeks |

N: animal number; Dosing volume was 10 μl/g; PTC124 and NMDI14 were given the first dose at randomization (tumor size ~50 mm$^3$), CTLA-4 and PD-1 antibody were given routinely when tumor size reached (75-100 mm$^3$), which was 3-4 days after giving PTC124 and NMDI14. If test compounds and antibodies were administrated on the same day, PTC124 and NMDI14 were given in the morning and antibodies given in the afternoon.

FACS analysis: Tumor cells were isolated from each treatment group and FACS analysis performed according to methods which are well known in the art. Reagents used for FACS analysis are shown in Table 4 below.

TABLE 4

Reagents used for FACS analysis of tumor cells.

| Marker | Cat. | | vender | Isotype | |
|---|---|---|---|---|---|
| CD45 | AF488 | 103122 | Biolegend | Rat IgG2b, k | |
| CD3 | APC-CY7 | 100222 | Biolegend | Armenian IgG1, k | Hamster |
| CD4 | BV510 | 100449 | Biolegend | Rat IgG2b, k | |
| CD8 | PE | 100708 | Biolegend | Rat IgG2a, k | |
| L/D dye | BUV395 | L34962 | Invitrogen | — | |

Immunohistochemistry (IHC): Formalin-fixed paraffin-embedded (FFPE) tissue from tumor samples were sectioned to 4 lim. Antigen retrieval (AR) was conducted at 100° C., in EDTA buffer, at pH 9.0 for 20 min. Primary antibody (diluted with validated concentration), RT 60 min+ secondary antibody (ready-to-use), RT 60 min+Bond Polymer Refine Detection. Antibodies and reagents used are shown in Table 5.

TABLE 5

Antibodies and reagents used in IHC experiments.

Primary Ab

| Antibodies | Company | Cat# | Type | Reactivity | Application | Concentration | Dilution |
|---|---|---|---|---|---|---|---|
| CD3 | Abcam | Ab5690 | Rb pAb | Hu, Ms, Rat | IHC-P | 0.2 mg/ml | 1:100 |
| CD8 | Abbiotec | 250596 | Rb pAb | Ms, Rat | IHC-P | 1 mg/ml | 1:400 |

Secondary Ab

| Antibodies | Company | Cat# | Detail information |
|---|---|---|---|
| Goat anti-Rb IgG | Leica | DS9800 | Anti-rabbit Poly-HRP-IgG (<25 μg/mL) containing 10% (v/v) animal serum in tris-buffered saline/0.09% ProClin ™ 950 (ready-to-use) |

Results:

After tumor cell inoculation, the animals were checked daily for morbidity and mortality as well as any effects of tumor growth and treatments on normal behavior such as mobility, visual estimation of food and water consumption, body weight gain/loss, eye/hair matting and any other abnormal effect. Tumor volumes were measured twice weekly at least in two dimensions using a caliper, and the volume expressed in mm$^3$ using the formula: V 0.5 a×b$^2$ where a and b are the long and short diameters of the tumor, respectively.

Mean tumor volume for each treatment group over the course of the study is shown in Table 6 while the percent inhibition of tumor volume is shown in Table 7.

Example 2: In Vivo Studies Using Amlexanox and Checkpoint Inhibitors

Animals and cell cultures were maintained as described in Example 1. C57BL/6 mice were inoculated subcutaneously at the right lower flank region with MC38 tumor cells (1×10$^6$) in 0.1 mL of PBS for tumor development. The treatments were started when the mean tumor size reaches approximately 50 mm$^3$. Compounds were administered and the animal numbers in each study group are shown in Table 8. The date of tumor cell inoculation was denoted as day 0. All the compounds were administered i.p.

TABLE 6

Mean tumor volume (mm$^3$) (+/−standard error of the mean)

| Group | Day 9 | Day 12 | Day 15 | Day 18 | Day 22 | Day 25 | Day 29 | Day 32 |
|---|---|---|---|---|---|---|---|---|
| 1 | 51.97 | 84.06 | 130.14 | 288.61 | 478.07 | 800.52 | 1258.55 | 1783.31 |
|   | (2.78) | (7.26) | (14.38) | (42.26) | (59.47) | (85.67) | (109.08) | (166.07) |
| 2 | 51.60 | 75.75 | 126.43 | 229.57 | 396.58 | 740.21 | 1203.80 | 1847.51 |
|   | (3.07) | (4.35) | (11.05) | (16.98) | (46.29) | (108.23) | (198.90) | (282.24) |
| 3 | 52.13 | 77.41 | 156.84 | 235.08 | 356.65 | 580.19 | 819.16 | 1186.59 |
|   | (2.66) | (5.02) | (17.03) | (18.74) | (34.77) | (73.20) | (92.78) | 167.50) |
| 4 | 51.98 | 69.50 | 148.03 | 201.18 | 338.87 | 502.47 | 737.46 | 997.16 |
|   | (2.61) | (3.13) | (4.64) | (14.54) | (39.46) | (66.04) | (103.25) | (125.74) |
| 5 | 51.99 | 86.86 | 162.86 | 226.06 | 290.45 | 421.74 | 543.10 | 811.76 |
|   | (2.75) | (7.40) | (13.78) | (24.42) | (34.86) | (69.42) | (94.42) | (133.83) |
| 6 | 52.09 | 67.76 | 130.84 | 208.29 | 310.79 | 469.30 | 653.87 | 891.94 |
|   | (2.94) | (3.77) | (10.70) | (16.82) | (27.96) | (40.94) | (56.30) | (78.27) |
| 7 | 52.03 | 82.86 | 129.45 | 231.22 | 369.67 | 610.15 | 808.24 | 1252.84 |
|   | (2.97) | (9.35) | (12.49) | (32.98) | (74.51) | (121.97) | (118.22) | (165.92) |
| 8 | 51.98 | 76.73 | 131.12 | 196.83 | 234.60 | 284.96 | 350.14 | 471.39 |
|   | (2.74) | (3.41) | (14.18) | (25.85) | (41.66) | (57.91) | (79.07) | (101.05) |

TABLE 7

Percent inhibition of tumor volume for each treatment group (negative values indicate an increase in tumor volume).

| Group | Day 9 | Day 12 | Day 15 | Day 18 | Day 22 | Day 25 | Day 29 | Day 32 |
|---|---|---|---|---|---|---|---|---|
| 2 | 0.70% | 9.88% | 2.85% | 20.46% | 17.05% | 7.53% | 4.35% | −3.60% |
| 3 | −0.31% | 7.90% | −20.52% | 18.55% | 25.40% | 27.52% | 34.91% | 33.46% |
| 4 | −0.03% | 17.31% | −13.74% | 30.29% | 29.12% | 37.23% | 41.40% | 44.08% |
| 5 | −0.04% | −3.34% | −25.14% | 21.67% | 39.25% | 47.32% | 56.85% | 54.48% |
| 6 | −0.23% | 19.38% | −0.54% | 27.83% | 34.99% | 41.38% | 48.05% | 49.98% |
| 7 | −0.12% | 1.43% | 0.53% | 19.88% | 22.67% | 23.78% | 35.78% | 29.75% |
| 8 | −0.02% | 8.71% | −0.75% | 31.80% | 50.93% | 64.40% | 72.18% | 73.57% |

Figure 2:
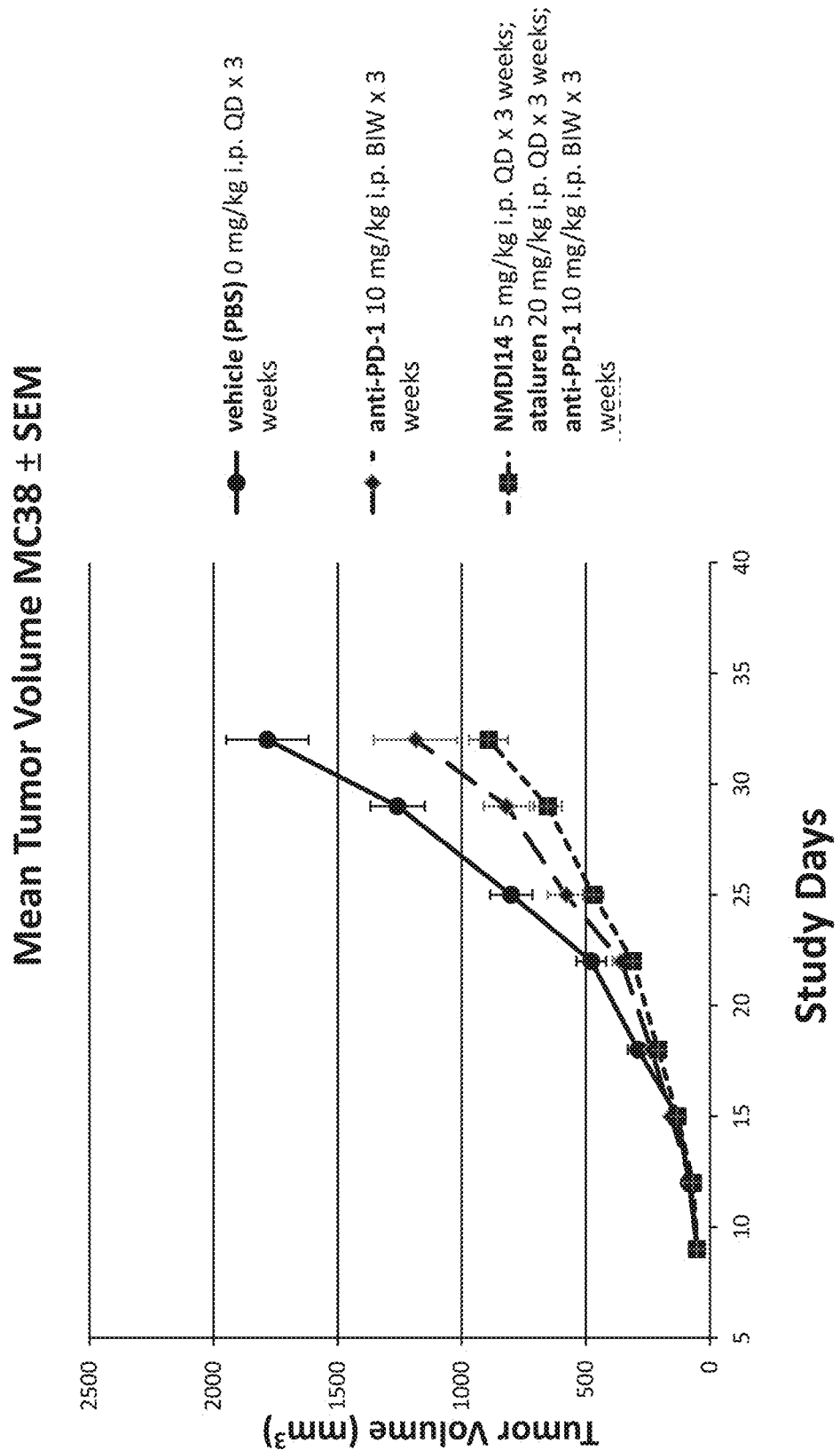
FIG. 2 depicts a graph comparing the effect of PTC124 (Ataluren) and NMDI14 and/or anti-PD-1 administration on tumor volume (mm3).

As shown in Table 7, the combination of PTC124 and a nonsense mediated decay inhibitor with anti-PD-1 and anti-CTLA-4 immunotherapy resulted in an almost 75% inhibition in tumor volume (see also FIG. 1), which is greater than the result achieved by either immunotherapy alone or their combination (FIG. 2).

Figure 3:
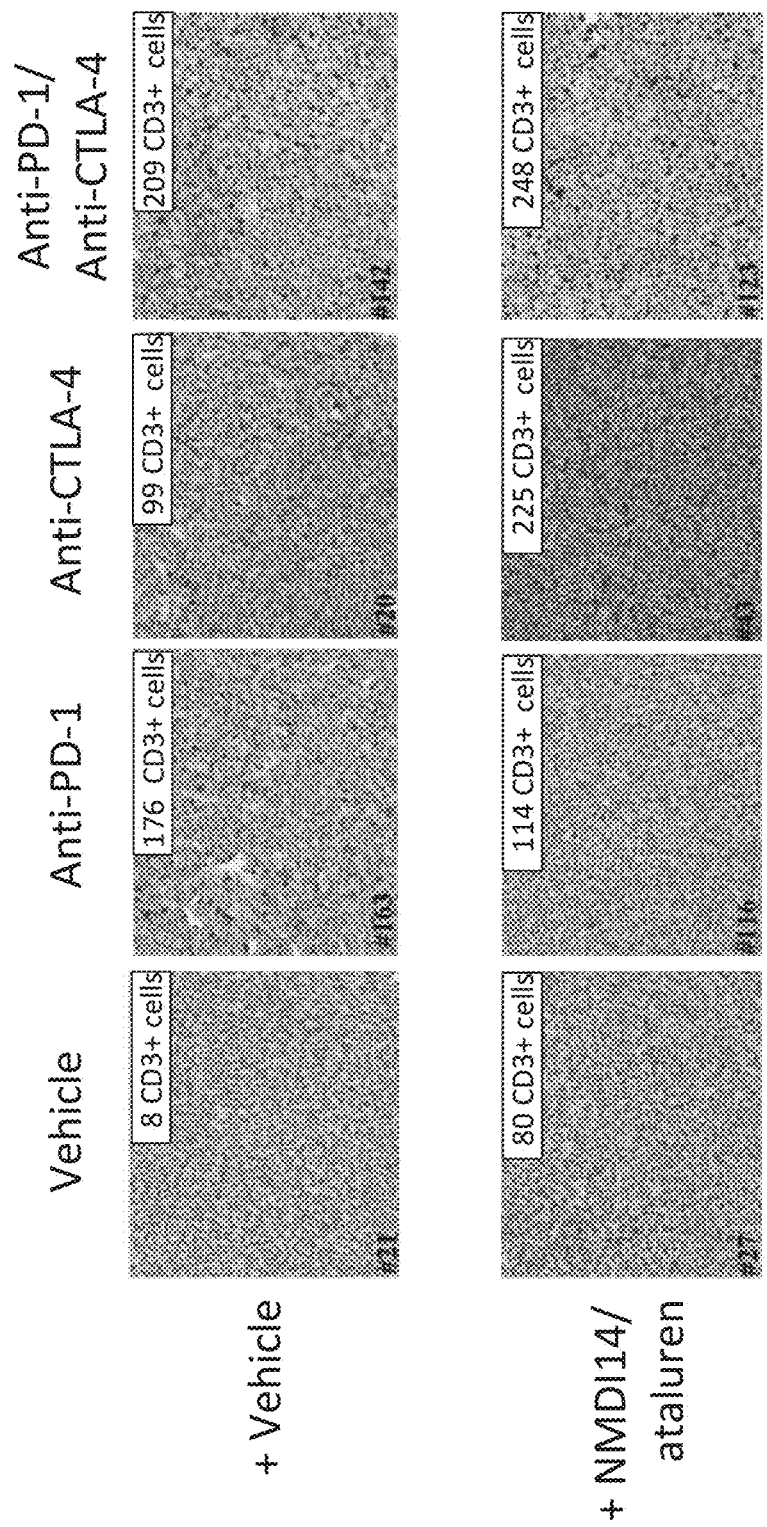
FIG. 3 depicts an image of a micrograph of sectioned tumor tissue showing immune cell infiltration following treatment.

As shown in FIG. 3, immunohistochemical analysis demonstrated that treatment with a PTC read-through inhibitor in combination with a compound that inhibits NMD resulted in significant numbers of CD3+ immune cells infiltrating tumor tissue. FIG. 3 also indicates that this effect was enhanced when treatment was combined with antibodies to PD-1 and to CTLA-4.

TABLE 8

| Group | Treatment | Dose per administration (if multiple dosings per day) | Dosing Schedule |
|---|---|---|---|
| Group-1 | NMDI14 | 5 mg/kg | QD × 3 Weeks |
|  | CTLA-4 | 10 mg/kg | BIW × 3 weeks |
|  | PD-1 | 10 mg/kg | BIW × 3 weeks |
| Group-2 | PTC124 | 20 mg/kg | QD × 3 Weeks |
|  | CTLA-4 | 10 mg/kg | BIW × 3 weeks |
|  | PD-1 | 10 mg/kg | BIW × 3 weeks |
| Group-3 | amlexanox | 20 mg/kg | QD × 3 Weeks |
|  | CTLA-4 | 10 mg/kg | BIW × 3 weeks |
|  | PD-1 | 10 mg/kg | BIW × 3 weeks |
| Group-4 | CTLA-4 | 10 mg/kg | BIW × 3 weeks |
|  | PD-1 | 10 mg/kg | BIW × 3 weeks |

TABLE 8-continued

| Group | Treatment | Dose per administration (if multiple dosings per day) | Dosing Schedule |
|---|---|---|---|
| Group-5 | Vehicle (vehicle 2) | — | QD × 3 Weeks |
| Group-6 | amlexanox | 10 mg/kg | QD × 3 Weeks |

After tumor cell inoculation, the animals were checked daily for morbidity and mortality as well as any effects of tumor growth and treatments on normal behavior such as mobility, visual estimation of food and water consumption, body weight gain/loss, eye/hair matting and any other abnormal effect. Tumor volumes were measured twice weekly at least in two dimensions using a caliper, and the volume expressed in mm3 using the formula: V=0.5 a×b2 where a and b are the long and short diameters of the tumor, respectively. Mean tumor volume for each treatment group over the course of the study is shown in Table 9, and the percent inhibition of tumor volume is shown in Table 10.

TABLE 9

| Group | 7 | 11 | 14 | 18 | 21 | 25 | 26 |
|---|---|---|---|---|---|---|---|
| Group 01 | 24.66 | 136.87 | 188.96 | 283.91 | 371.24 | 633.46 | 956.83 |
| Group 02 | 19.21 | 52.15 | 84.22 | 104.65 | 115.74 | 203.53 | 273.39 |
| Group 03 | 10.20 | 43.28 | 45.66 | 73.10 | 73.87 | 166.47 | 253.56 |
| Group 04 | 17.68 | 79.43 | 92.30 | 107.95 | 167.52 | 166.22 | 223.44 |
| Group 05 | 11.86 | 112.32 | 205.99 | 677.38 | 1122.72 | 1982.23 | 1612.43 |
| Group 06 | 17.22 | 145.47 | 286.64 | 982.03 | 1830.00 | 2816.94 | 3301.20 |

TABLE 10

Percent inhibition of tumor volume for each treatment group (negative values indicate an increase in tumor volume).
Mean % Inhibition, Tumor Volume MC38

| | Dates/Study Days | | | | | | |
|---|---|---|---|---|---|---|---|
| Group | Mar. 17, 2017 7 | Mar. 21, 2017 11 | Mar. 24, 2017 14 | Mar. 28, 2017 18 | Mar. 31, 2017 21 | Apr. 4, 2017 25 | Apr. 7, 2017 28 |
| Group 01 | −107.92 | −21.85% | 8.26% | 58.08% | 66.93% | 68.04% | 40.65% |
| Group 02 | −61.97% | 53.57% | 59.11% | 84.55% | 89.69% | 89.73% | 83.04% |
| Group 03 | 13.99% | 61.46% | 77.82% | 89.02% | 93.42% | 91.60% | 84.27% |
| Group 04 | −49.07% | 29.28% | 55.19% | 84.06% | 85.07% | 91.61% | 86.14% |
| Group 05 | — | — | — | — | — | — | — |
| Group 06 | −45.19% | −29.51% | −39.15% | −44.97% | −63.00% | −42.11% | −104.74% |

Figure 4:
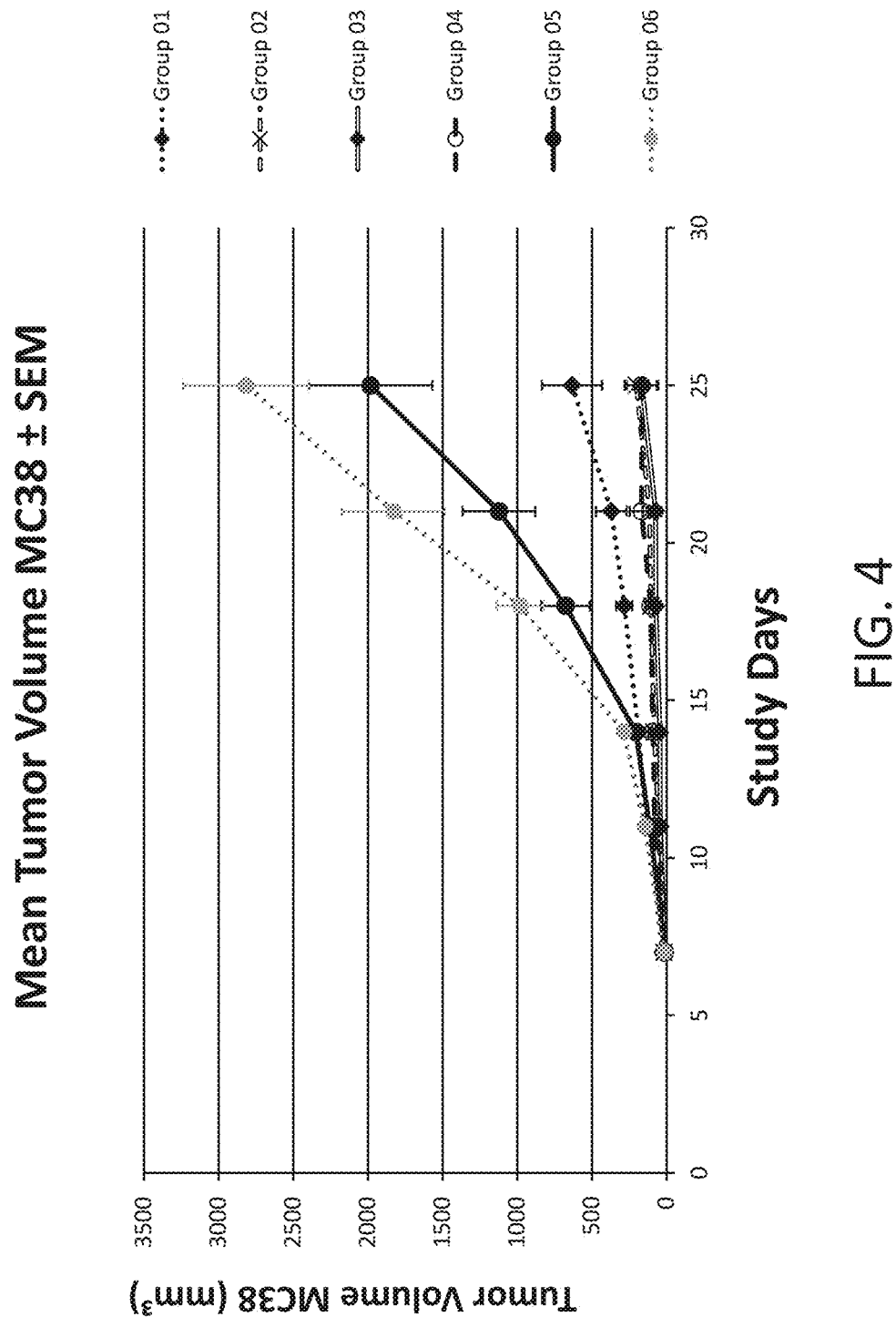
FIG. 4 depicts a graph comparing the effect of administration of amlexanox in combination with anti-PD-1 antibody and anti-CTLA-4 antibody on tumor volume (mm3).

Mean % Inhibition = (mean(C) − mean(T))/mean(C) * 100%
T - current group value
C - control group value As shown in Table 10, the combination of amlexanox with anti-PD-1 and anti-CTLA-4 immunotherapy resulted in an almost 84% inhibition in tumor volume (see also FIG. 4), which was comparable to PTC124 and PD-1/CTLA-4 combination.

Example 3: Xenograft Studies with Other Cancer Cell Lines

Syngeneic immune competent tumor models can be created with murine cancer cell lines, examples include pancreatic (Pan02), prostate (RM1), colon (CT-26, Colon-26, MC38-26), kidney (Renca), bladder (MBT-2), lung (LL/2, KLN205), melanoma (B16BL6, B16F10, S91), breast (4T1, EMT6, JC), fibrosarcoma (WEHI-164), leukemia (C1498, L1210), liver (H22, Hepal-6), lymphoma (A20, EL-4, E.G&-OVA, L5178-R, P388D1), mastocytoma (P815), myeloma (MPC-11), neuroblastoma (Neuro-2a) among others. As shown in Examples 1 and 2, mice will receive a suspension of tumor cells injected subcutaneously which develops into a tumor approximately 4-6 weeks after injection.

To test the efficacy of treatments on early established mouse tumors, cohorts of 10 mice per group will receive drugs (or sham controls) beginning on days 3-7 or when tumors are palpable. Drugs will be given on a daily basis, twice daily basis, several times a week or dosed continuously until mice are sacrificed at 4-6 weeks or when tumors achieve 3-5 cm in size or become ulcerated. During treatment, tumor volume is determined using three-dimensional measurements by calipers three times a week. Tumors will be collected after sacrificing and will be weighed to determine final tumor volume, as shown in Examples 1 and 2.

Example 4: Combination of Amelxanox with an Epigenetic Modulatory Drug

This Example shows administration of amlexanox and an epigenetic modulatory drug. Addition of one or more epigenetic modulatory drug has the potential of enhancing immune recognition of neoantigens.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Treatment of tumors with epigenetic modulators can remove repression of genes involved in the immune response. Combination with RTC and NMDI with an epigenetic modulatory drug would enhance recognition of neoantigens. Non-limiting examples of epigenetic modulatory drugs include, without limitation, HDAC inhibitors, azocytidine, BET inhibitors, EZH2 inhibitors, and/or dot1L inhibitor (e.g., pinometostat), and DNA methyltransferase (DNMT) inhibitors.

Example 5: Combination of Amlexanox with Radiation Therapy

This Example shows the effect of treatment of tumors in syngeneic immune competent mice with a combination of amlexanox and radiation therapy. Treatment with amlexanox drug prior to radiation therapy (RT) would increase the expression of neoantigens in the tumor prior to immuno stimulatory cell death, leading to enhanced neoantigen presentation.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Continual treatment with amlexanox during radiation therapy (RT) targeted to a tumor has the potential to generate neoantigens via mutagenesis and DNA damage. Release of these antigens during cell death in conjunction with proinflammatory signals that trigger the immune response to activate tumor-specific T cells. Radiation therapy can affect the tumor microenvironment and enhance infiltration of activated T-cells, and overcome barriers of tumor rejection. Combination of amlexanox with immunotherapy agent and RT would enhance effects of radiation on both priming (antigen presentation) and effector phases of the immune response in an individual patient, by enhancing expression of neoantigens.

Example 6: Combination of Amlexanox with Chemotherapy

This Example shows the effect of treatment of tumors in syngeneic immune competent mice with a combination of RTCs and NMDIs and chemotherapy. Treatment with an RTC and NMDI drug prior to chemotherapy would increase the expression of neoantigens in the tumor prior to immunostimulatory cell death, leading to enhanced neoantigen presentation.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Continual treatment with amlexanox during chemotherapy has the potential to generate neoantigens via mutagenesis and DNA damage, and release of these antigens during cell death in conjunction with proinflammatory signals that trigger the immune response to activate tumor-specific T cells. Chemotherapy can affect the tumor microenvironment and enhance infiltration of activated T-cells, and overcome barriers of tumor rejection. Combination of amlexanox and immunotherapy agent (Example 1) with chemotherapy would enhance effects of chemotherapy on both priming and effector phases of the immune response in an individual patient, by enhancing expression of neoantigens.

Example 7: Combination of Amlexanox of Oncolytic Viruses

This Example shows the effect of treatment of tumors in syngeneic immune competent mice with a combination of amlexanox and oncolytic viruses.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Other approaches to induce immunogenic cell death include the use of oncolytic viruses to selectively kill tumor cells. Thus, prior treatment of patients with amlexanox would enable oncolytic viruses to improve antigen presentation of the induced neoantigens, and subsequently enhance T cell responses.

Example 8: Combination of Amlexanox with Vaccine Therapy

This Example shows the effect of treatment of tumors in syngeneic immune competent mice with a combination of amlexanox and vaccine therapy.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Neoantigen vaccination is emerging as a potentially effective vaccine approach in cancer. To date, these neoantigens have included amino acid substitutions, whereas amlexanox will broaden the scope of neoantigens beyond single amino acid substitutions. Abnormal peptides generated from amlexanox or DNA or RNA encoding those products, represent components of personalized vaccines. Transcriptional profiling of patient tumors treated with amlexanox provides candidate abnormal read-through proteins that could be used to generate such vaccines. Whole tumors treated with amlexanox may also be used as the basis for whole-cell vaccines. Such vaccines against induced neoantigens can be combined with any of the agents in these Examples, in addition to other vaccines.

Example 9: Combination of Amlexanox with CAR-T Cells or Patient-Derived Tumor Infiltrating Lymphocytes (TILs)

This Example shows the effect of treatment of tumors in syngeneic immune competent mice with a combination of amlexanox and CAR-T cells or patient-derived tumor infiltrating lymphocytes As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

T cells that are elicited in patients treated with amlexanox will be induced that recognize the neoantigens generated by these drugs. These specific T cells could be expanded ex vivo and re-infused into patients directly, or their TCRs could be cloned and used to engineer CAR-T cells for re-infusion.

Example 10: Combination of Amlexanox and Immune Modulators

This Example shows the effect of treatment of tumors in syngeneic immune competent mice with a combination of amlexanox and immune modulators, such as CDNs, TLR agonists, TNFR superfamily agonists, and epigenetic modulatory compounds.

As shown in Examples 1 and 2, mice will receive a suspension of tumor cells injected subcutaneously which develops into a tumor approximately 4-6 weeks after injection. Administration of the drugs, assessment of tumor size, intratumoral immune response, CD4 and CD8 effector T cell responses, and Treg response will be performed as described above.

Other approaches to induce immunogenic cell death include the use of immune modulators, such as CDNs, TLR agonists, TNFR superfamily agonists, and epigenetic modulatory compounds to selectively kill tumor cells. Thus, prior treatment of patients with amlexanox would enable immune modulators to improve antigen presentation of the induced neoantigens, and subsequently enhance T cell responses.

What is claimed is:

1. A method of treating cancer in a subject in need thereof comprising administering a therapeutically effective amount of amlexanox and a therapeutically effective amount of at least one checkpoint inhibitor selected from the group consisting of anti-PD-1 antibodies, anti-PD-L1 antibodies, anti-CTLA-4 antibodies, anti-A2AR antibodies, anti-KIR antibodies, anti-LAG3 antibodies, anti-B7-H3 antibodies, and combinations thereof, wherein the cancer is selected from the group consisting of colon carcinoma.

2. The method claim 1, wherein the method comprises administering amlexanox in combination with anti-PD-1 and anti-CTLA-4 antibodies.

3. The method claim 1, wherein the method comprises administering amlexanox in combination with anti-PD-L1 and anti-CTLA-4 antibodies.

4. The method of claim 1, wherein amlexanox is administered at a dose from about 1 mg/kg to 50 mg/kg daily.

5. The method of claim 1, wherein the checkpoint inhibitor is administered at a dose from about 3 mg/kg to about 10 mg/kg every 3 days.

6. The method of claim 1, wherein route of administration is selected from the group consisting of oral, topical, subcutaneous, intramuscular, intraperitoneal, intrathecal, transdermal, and intravenous injection.

* * * * *